(12) United States Patent
Drake et al.

(10) Patent No.: US 9,867,964 B2
(45) Date of Patent: Jan. 16, 2018

(54) INTERVENTIONAL MEDICAL SYSTEMS, ASSEMBLIES, AND CONSTRUCTION METHODS

(71) Applicant: Medtronic, Inc., Minneapolis, MN (US)

(72) Inventors: Ronald A Drake, St. Louis Park, MN (US); Lester O Stener, Hudson, WI (US); Kenneth C Gardeski, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 39 days.

(21) Appl. No.: 14/711,010

(22) Filed: May 13, 2015

(65) Prior Publication Data

US 2016/0310703 A1 Oct. 27, 2016

Related U.S. Application Data

(60) Provisional application No. 62/151,771, filed on Apr. 23, 2015.

(51) Int. Cl.
*A61M 25/01* (2006.01)
*A61N 1/375* (2006.01)
(Continued)

(52) U.S. Cl.
CPC ..... *A61M 25/0147* (2013.01); *A61B 17/3468* (2013.01); *A61M 25/0012* (2013.01);
(Continued)

(58) Field of Classification Search
CPC .......... A61M 25/0147; A61M 25/0012; A61M 25/0138; A61B 17/3468;
(Continued)

(56) References Cited

U.S. PATENT DOCUMENTS 4,233,734 A 11/1980 Bies
4,322,885 A 4/1982 Osada
(Continued)

FOREIGN PATENT DOCUMENTS

| EP | 0254701 A1 | 1/1988 |
|---|---|---|
| EP | 176326 | 11/2006 |
| EP | 2465568 | 6/2012 |

OTHER PUBLICATIONS (PCT/US2016/026370) PCT Notification of Transmittal of the International Search Report and the Written Opinion of the International Searching Authority, dated Sep. 29, 2016, 13 pages.
(Continued)

*Primary Examiner* — Paula J Stice

(57) ABSTRACT

A catheter for delivering a medical device to an implant site within a receptacle of a distal-most portion thereof, includes a coiled spring member, which has one or more proximal turns, secured to a shaft proximal portion, one or more distal turns, secured to the distal-most portion, and a plurality of open-pitch turns that extend between the proximal and distal turns and are, preferably, pre-loaded by longitudinal compression prior to forming a sheath thereover. A deflection assembly pull wire extends through a lumen of the shaft proximal portion and alongside the plurality of open-pitched turns of the spring member, wherein a pull wire proximal end extends proximally out from a proximal opening of the lumen of the proximal portion and into a handle of the catheter, for coupling to a control member subassembly, and a pull wire distal end is secured to the shaft distal-most portion.

22 Claims, 17 Drawing Sheets

(51) Int. Cl.
  *A61B 17/34* (2006.01)
  *A61M 25/00* (2006.01)
  *A61N 1/05* (2006.01)
  *A61B 17/00* (2006.01)

(52) U.S. Cl.
  CPC ......... *A61M 25/0138* (2013.01); *A61N 1/057* (2013.01); *A61N 1/3756* (2013.01); *A61B 2017/00323* (2013.01); *A61N 2001/0578* (2013.01)

(58) Field of Classification Search
  CPC .......... A61B 2017/00323; A61N 1/057; A61N 1/3756; A61N 2001/0578
  See application file for complete search history.

(56) References Cited

U.S. PATENT DOCUMENTS

| | | |
|---|---|---|
| 5,666,970 A | 9/1997 | Smith |
| 5,702,373 A | 12/1997 | Samson |
| 6,146,338 A | 11/2000 | Gardeski et al. |
| 6,599,296 B1 | 7/2003 | Gillick et al. |
| 7,419,477 B2 | 9/2008 | Simpson et al. |
| 7,497,853 B2 | 3/2009 | Fischer et al. |
| 7,678,074 B2 | 3/2010 | Fischer et al. |
| 7,993,384 B2 | 8/2011 | Wu et al. |
| 8,177,773 B2 | 5/2012 | Ovcharchyn et al. |
| 8,206,343 B2 | 6/2012 | Racz |
| 8,676,290 B2 | 3/2014 | Tegg |
| 8,706,260 B2 | 4/2014 | Stewart et al. |
| 8,721,587 B2 | 5/2014 | Berthiaume et al. |
| 8,784,468 B2 | 7/2014 | Gerdts et al. |
| 8,790,386 B2 | 7/2014 | Dwork |
| 8,911,487 B2 | 12/2014 | Bennett et al. |
| 8,920,432 B2 | 12/2014 | Drake et al. |
| 8,926,588 B2 | 1/2015 | Berthiaume et al. |
| 2006/0264819 A1 | 11/2006 | Fischer et al. |
| 2012/0158021 A1 | 6/2012 | Morrill |
| 2012/0323254 A1 | 12/2012 | Bonde et al. |
| 2013/0012925 A1 | 1/2013 | Berthiaume et al. |
| 2013/0079798 A1 | 3/2013 | Tran et al. |
| 2013/0103047 A1 | 4/2013 | Steingisser et al. |
| 2013/0131667 A1 | 5/2013 | Jenson et al. |
| 2013/0131693 A1 | 5/2013 | Berthiaume et al. |
| 2014/0052109 A1 | 2/2014 | Organ et al. |
| 2014/0074114 A1 | 3/2014 | Khairkhahan et al. |
| 2014/0228800 A1 | 8/2014 | Rezac et al. |
| 2014/0243844 A1 | 8/2014 | Clancy et al. |
| 2014/0336456 A1 | 11/2014 | Demers et al. |
| 2015/0246205 A1 | 9/2015 | Schaeffer |

OTHER PUBLICATIONS

U.S. Appl. No. 14/039,937, filed Sep. 27, 2013, 32pp.

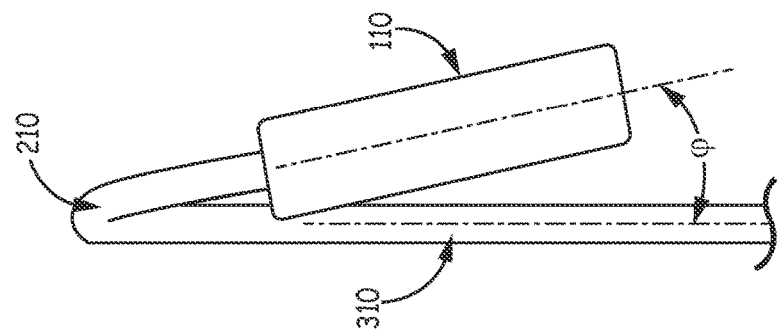
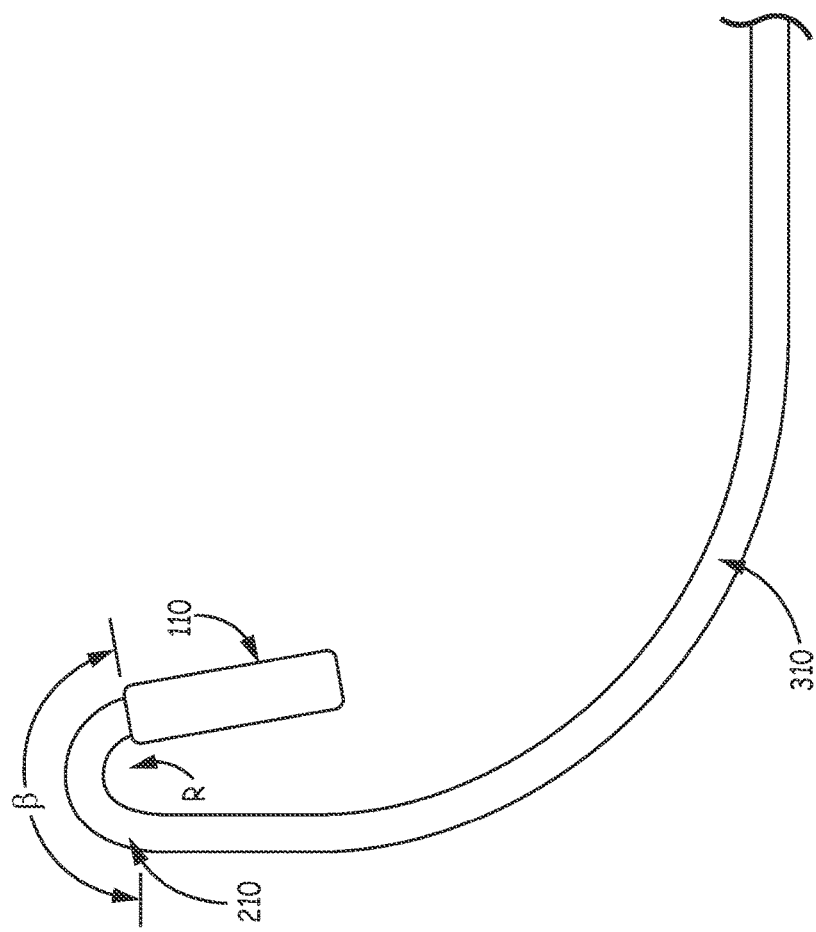

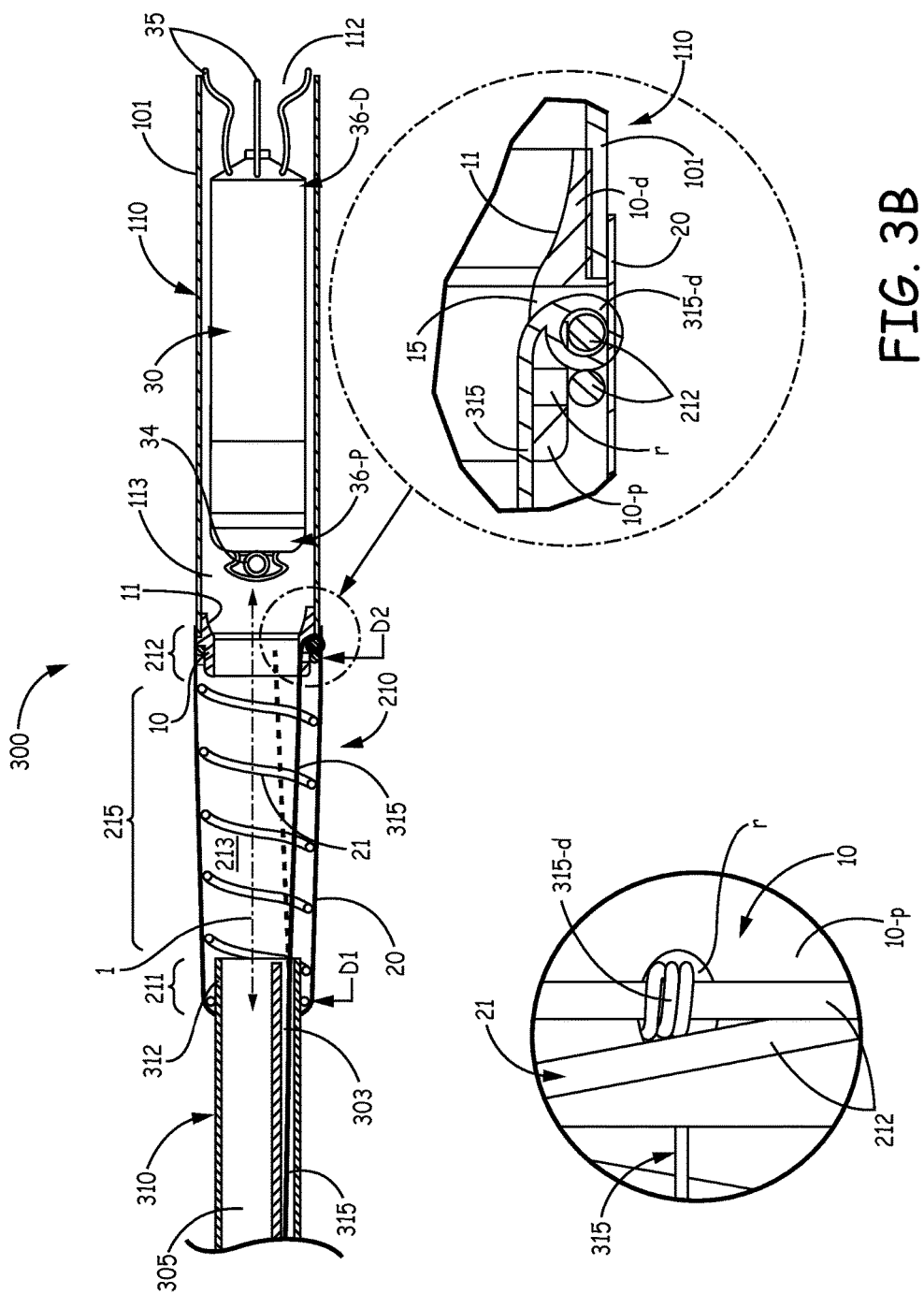

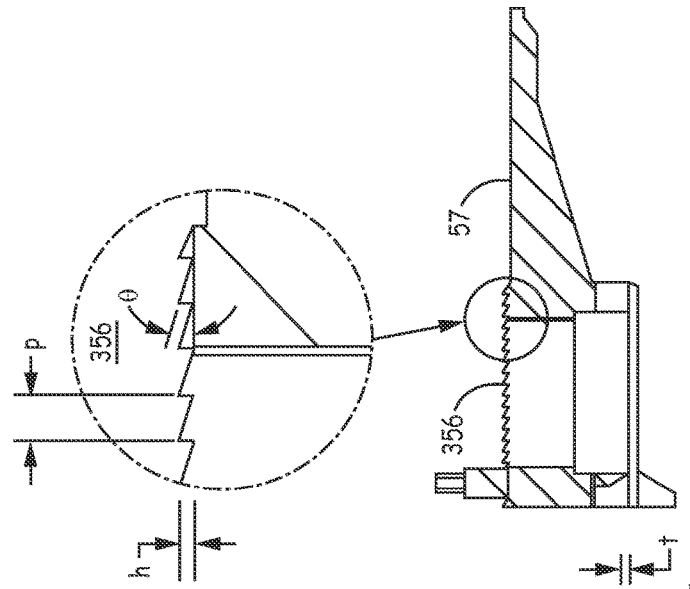
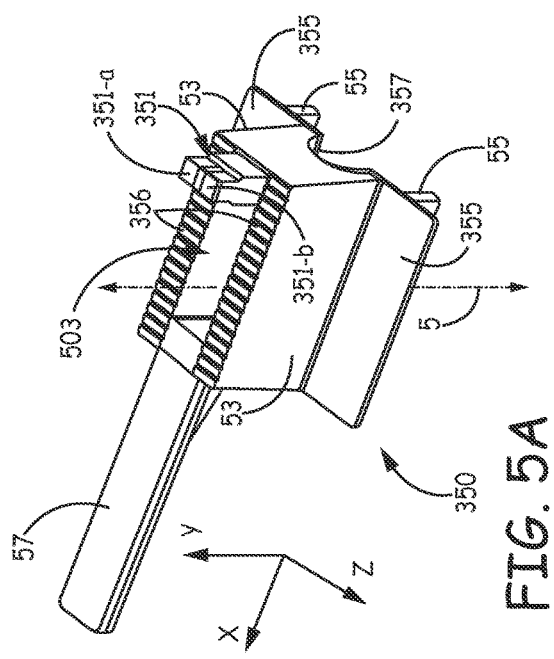
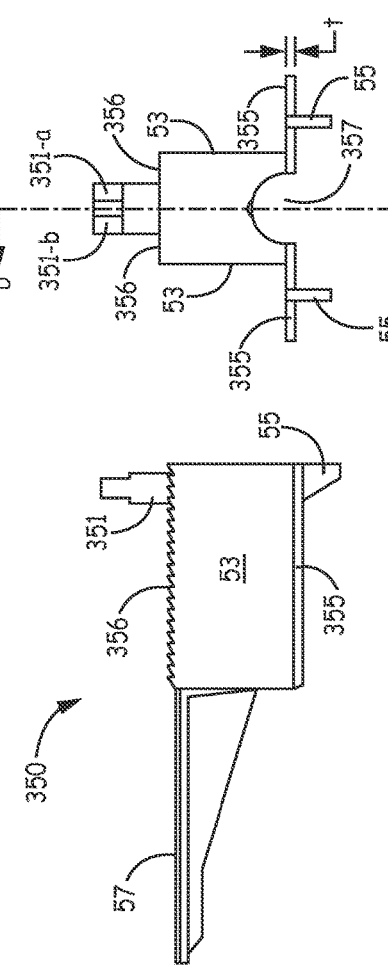

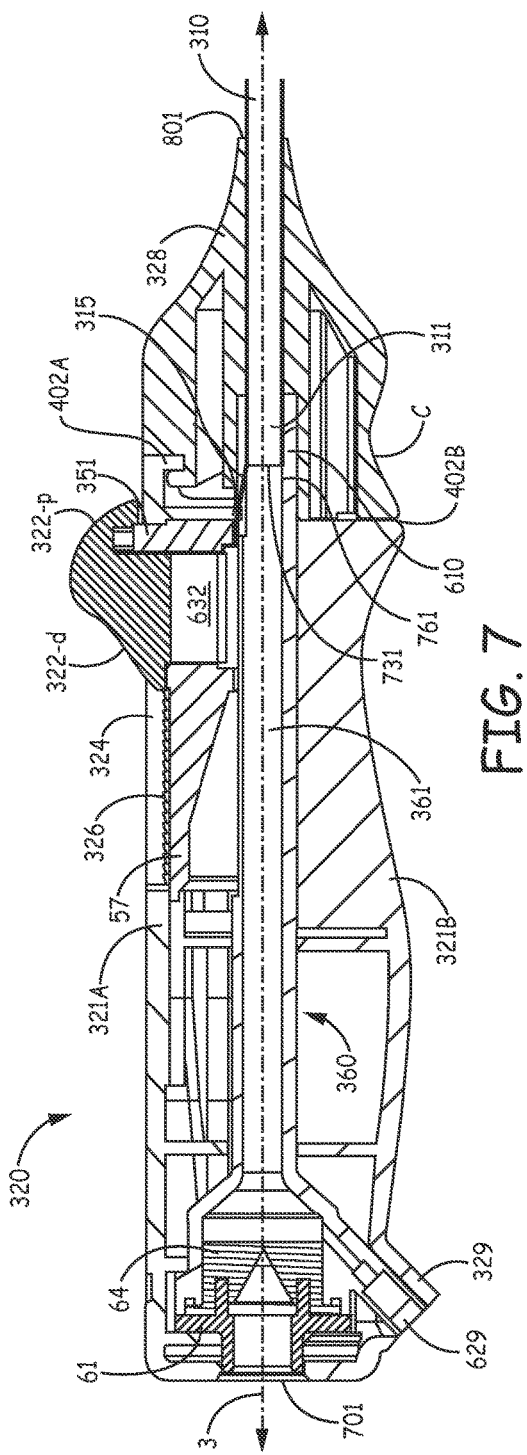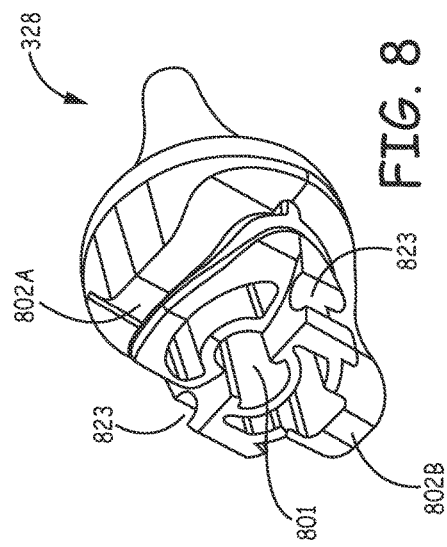
FIG. 7
FIG. 8

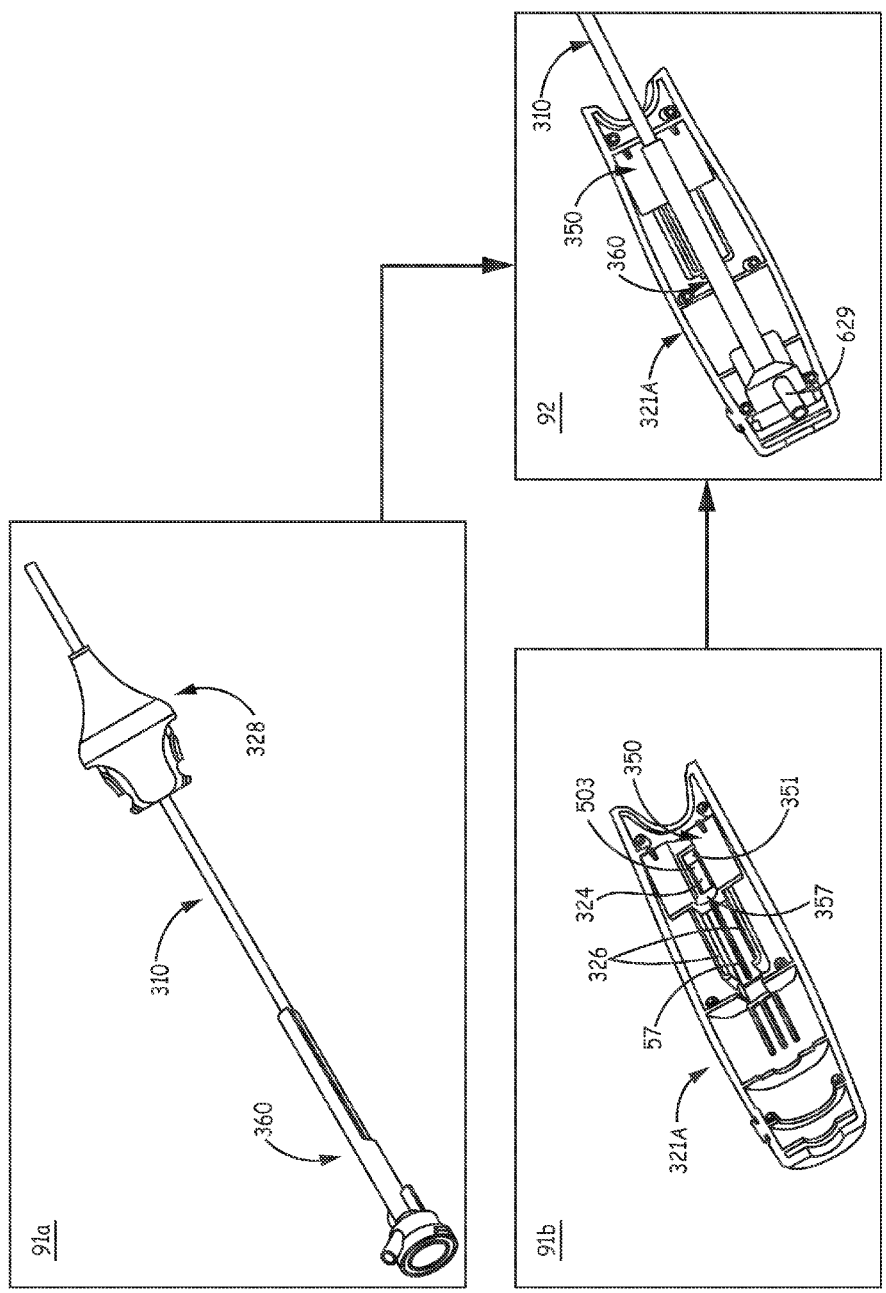

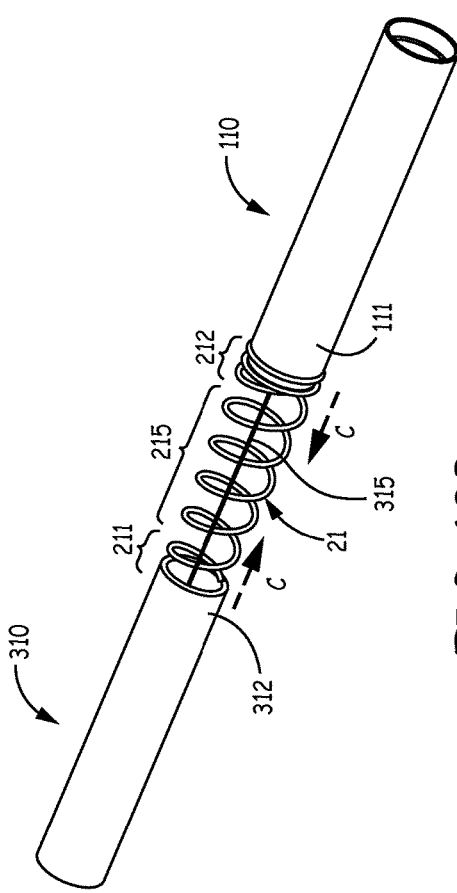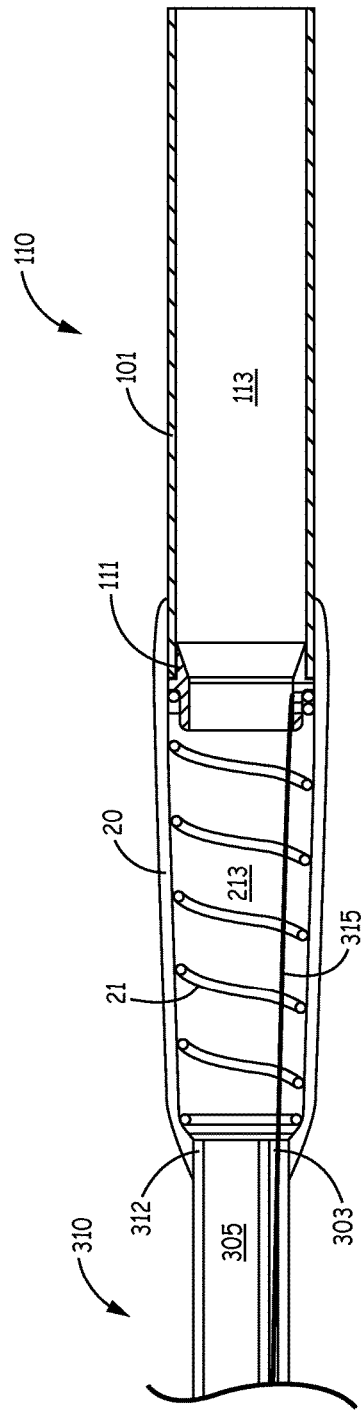

INTERVENTIONAL MEDICAL SYSTEMS, ASSEMBLIES, AND CONSTRUCTION METHODS

CROSS-REFERENCE TO RELATED APPLICATIONS

The present application claims priority to the U.S. Provisional Patent Application having the Ser. No. 62/151,771, which was filed on Apr. 23, 2015, and which is incorporated by reference herein. The present application is related to the commonly assigned U.S. patent application Ser. No. 14/694,579, entitled ASSEMBLIES AND METHODS FOR DEFLECTABLE SHAFT CATHETERS, which was filed on Apr. 23, 2015, and which is incorporated by reference herein.

FIELD OF THE DISCLOSURE

The present invention pertains to interventional medical systems, and more particularly to assemblies of deflectable shaft catheters for the deployment of relatively compact implantable medical devices.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package for implant in close proximity to the pacing site, for example, within the right ventricle RV of the heart. With reference to FIG. 1A, such a device 30 is illustrated, wherein an hermetically sealed housing 36, preferably formed from a biocompatible and biostable metal such as titanium, contains an electronic controller and associated power source (not shown), to which at least one electrode 31 is coupled, for example, by a hermetic feedthrough assembly (not shown) like those known to those skilled in the. Housing 36 may be overlaid with an insulative layer, for example, medical grade polyurethane, parylene, or silicone, and a portion of the insulation layer may be removed to form another electrode 32, for example, to provide bipolar pacing and sensing in conjunction with electrode 31.

FIG. 1A shows device 30 having been delivered to an implant site by an operator, via a standard guiding catheter 150 known to those skilled in the art, which the operator has maneuvered up through the inferior vena cava IVC and across the right atrium RA into the right ventricle RV. The delivered device 30 is shown fixed at the implant site by a fixation member 35 thereof. Although catheter 150 may be suitable in the illustrated instance, there is a need for more versatile types of catheters capable of delivering implantable medical devices, like device 30, to some alternative implant sites, for example, like a site S of FIG. 1A, located on a septal wall of the right ventricle RV.

SUMMARY

An interventional medical system, according to some embodiments disclosed herein, includes an implantable medical device and an improved catheter for delivering the device to an implant site, for example, within a receptacle formed by a sidewall of a distal-most portion of a shaft thereof, wherein a coiled spring member, which has one or more proximal turns secured to a proximal portion of the catheter shaft, and has one or more distal turns secured to the distal-most portion of the shaft, defines a transition lumen of the catheter shaft. The transition lumen is preferably in fluid communication with the receptacle of the catheter shaft distal-most portion and with one or more lumens of the catheter shaft proximal portion. The improved catheter further includes a deflection assembly in which a pull wire extends within one of the lumens of the catheter shaft proximal portion; a distal end of the pull wire, which extends out from a distal opening of the lumen, is secured to the shaft distal-most portion, and a proximal end of the pull wire extends proximally out from a proximal opening of the lumen, preferably, at a proximal terminal end of the shaft, and into a handle of the catheter for coupling to a control member subassembly. According to some preferred embodiments, the coiled spring member is longitudinally compressed, or pre-loaded, before forming a sheath thereover, which may secure the pre-load while allowing for some additional longitudinal compression of the spring member. In some embodiments, the pre-load of coiled spring member may be secured by a backbone member coupled to the spring member, which may limit additional longitudinal compression more than the sheath.

According to some embodiments and methods, the distal opening of the lumen of the proximal portion of the catheter shaft, from which the pull wire extends, is circumferentially offset from the attached distal end of the pull wire, wherein the offset may be between approximately 45 degrees and approximately 90 degrees. The distal end of the pull wire, in some embodiments and methods, is formed in one or more loops that extend around the one or more distal turns of the coiled spring member, wherein the one or more distal turns may be coupled to a collar of the distal-most portion of the catheter shaft, and a recess formed in a sidewall of the collar may receive the distal end of the pull wire.

In the deflection assembly of the improved catheter, according to some embodiments, the proximal end of the pull wire is secured to a post of the control member subassembly, for example, which extends through an elongate slot of a shell of the handle; and wherein an engagement feature of the control member subassembly, which is supported by an elastically deformable support of the subassembly resting on a railway of the handle, confronts a mating feature of the handle for interlocking engagement therewith, when the elastically deformable support is undeformed. The interlocking engagement prevents the control member subassembly from moving along a length of the handle slot, but when the operator applies a particular force vector to an operator interface of the control member subassembly, which may be coupled to the post, the elastically deformable support deforms against the railway of the handle so that the engagement feature of the control member subassembly moves out from the interlocking engagement with the mating feature of the handle, and the control member subassembly moves along the length of the handle slot.

BRIEF DESCRIPTION OF THE DRAWINGS

The following drawings are illustrative of particular embodiments of the present invention and therefore do not limit the scope of the invention. The drawings may or may not be to scale, and are intended for use in conjunction with the explanations in the following detailed description. Embodiments will hereinafter be described in conjunction with the appended drawings wherein like numerals denote like elements, and:

FIGS. 1C-D are a plan view and a corresponding end view of a portion of the catheter, according to some embodiments;

FIG. 3B is a longitudinal cross-section view through section line A-A of FIG. 3A, with an enlarged detail view, according to some embodiments;

FIG. 3C is an enlarged plan view of a portion of a catheter shown in FIG. 3A, according to some embodiments;

FIG. 5A is a perspective view of a slider component of a control member subassembly, according to some embodiments;

FIG. 5B is an elevation view of the slider component, according to some embodiments;

FIG. 5C is an end view of the slider component, according to some embodiments;

FIG. 5D is a cross-section view through section line D-D of FIG. 5C, according to some embodiments;

FIG. 7 is a longitudinal cross-section view of a deflection assembly, according to some embodiments;

FIG. 8 is a perspective view of a strain relief element that may be employed in conjunction with the deflection assembly in a deflectable shaft catheter, according to some embodiments;

FIGS. 9B-E are schematics outlining some methods for assembling a deflection assembly for a catheter, such as the catheter shown in FIG. 3A; and FIGS. 10A-C are schematics outlining some construction methods for a deflectable catheter shaft, according to some embodiments of the present invention.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1A:
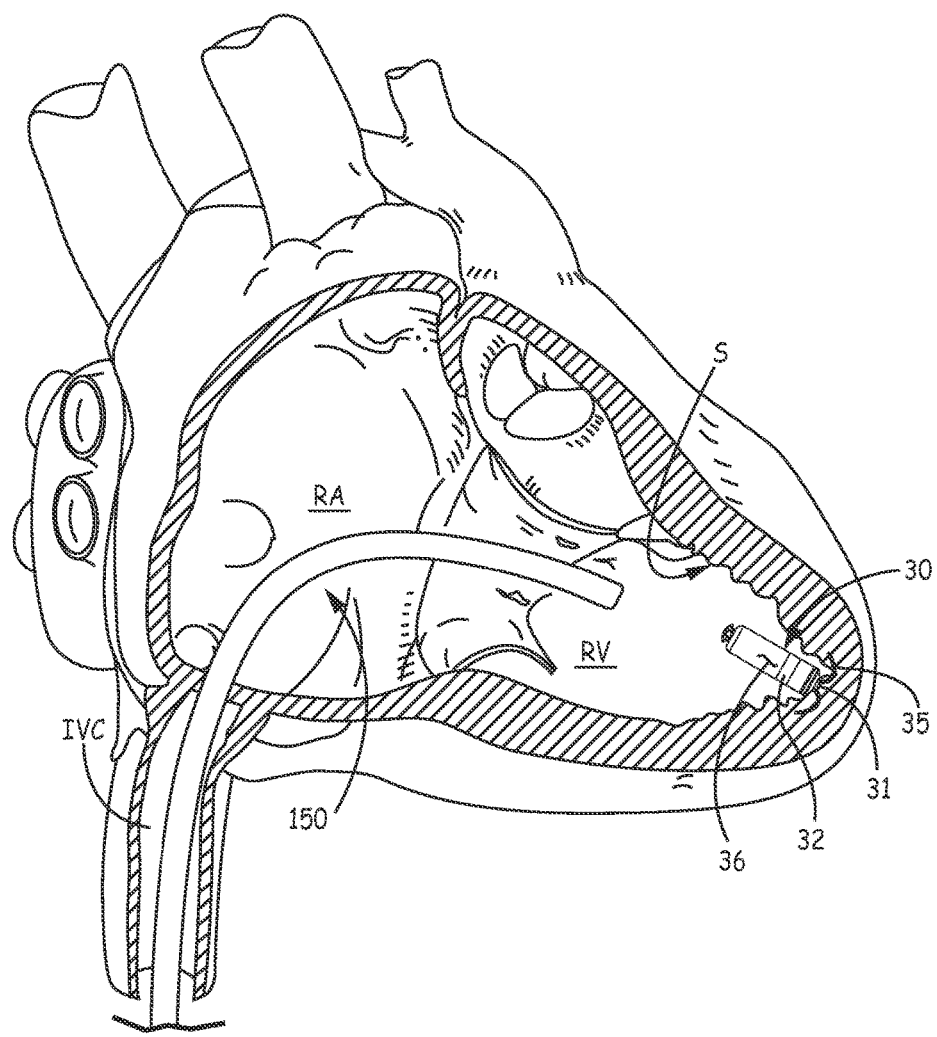
FIG. 1A is a schematic showing an example of an implanted medical device for cardiac stimulation.
Figure 1B:
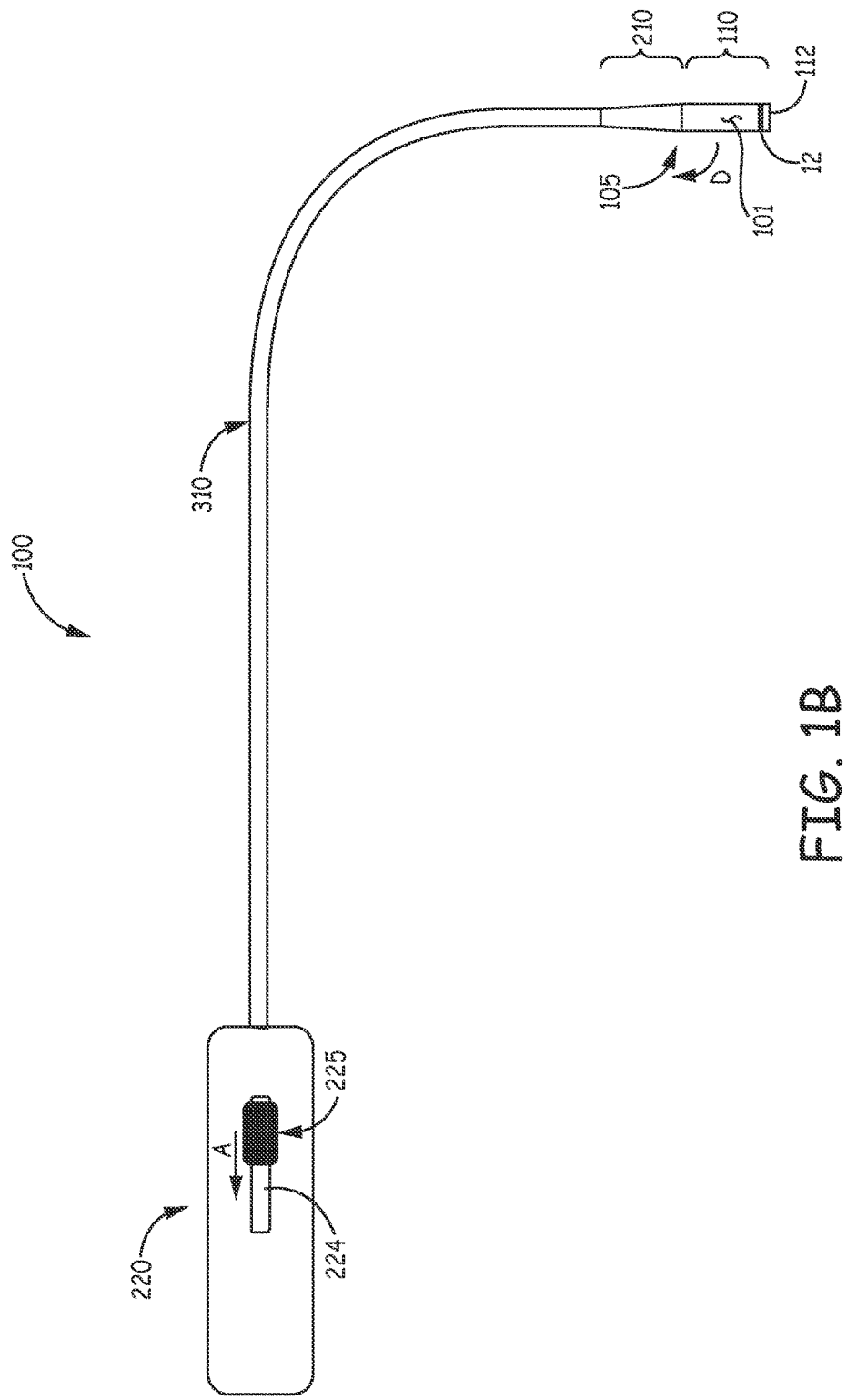
FIG. 1B is a plan view of an exemplary deflectable shaft catheter, according to some embodiments.

FIG. 1B is a plan view of an exemplary deflectable shaft catheter 100, according to some embodiments. FIG. 1B illustrates an elongate deflectable shaft of catheter 100 including a proximal portion 310, which is secured to a handle 220, a distal-most portion 110, and a deflectable segment 210 extending between proximal portion 310 and distal-most portion 110. According to the illustrated embodiment, a sidewall 101 of shaft distal-most portion 110, for example, formed from a medical grade polyether block amide (e.g., PEBAX® 7233 SA-01), defines a receptacle 113 (shown in FIG. 3B) that has a distal opening 112 defined by a distal terminal end of sidewall 101, wherein receptacle 113 is sized to contain an implantable medical device, for example, device 30, so that catheter 100 can deliver the device to an implant site. Sidewall 101 is shown having a radiopaque marker band 12 attached thereto, in proximity to opening 112, according to some embodiments, wherein, marker band 12 may be formed from a gold foil for example, having a thickness of approximately 10 microns and being secured around sidewall 101 by a reflow of the material of sidewall 101 thereover. It should be noted that, in some alternate embodiments, distal-most portion 110 may be formed from a medical grade metal material, such as stainless steel. Although shaft proximal portion 310 is shown having a pre-formed bend, alternate embodiments need not include the pre-formed bend. In either case, shaft proximal portion 310, for example, being formed from a stainless steel braid-reinforced polyether block amide tube (e.g., PEBAX®), has a flexibility to generally conform to a patient's venous system when being passed therethrough to deliver the implantable medical device.

FIG. 1B further illustrates catheter 100 including a control member subassembly 225 that, when moved in the general direction of arrow A, causes shaft deflectable segment 210 to deflect, or bend, per arrow D, for example, via a pull wire 115 (shown in FIG. 2) that extends distally from control member subassembly 225, along a length of the catheter shaft, to a distal end thereof anchored at a location 105, just distal to segment 210. FIG. 1C is a plan view a portion of the catheter shaft that shows segment 210 pulled, or deflected into a 'knuckle bend' by control member subassembly 225, according to some preferred embodiments, wherein a radius R of the bend may be as tight as approximately 5 mm and extend over an angle β of up to approximately 180 degrees. Embodiments of an improved construction for catheter shaft deflectable segment 210, which are described in greater detail below (FIGS. 3A-D), facilitate such a 'knuckle bend'. With reference to FIG. 1D, which is an end view of the portion shown in FIG. 1C, some construction embodiments may also provide for an offset of distal-most portion 110 by an angle φ, which may be between approximately 20 degrees and approximately 40 degrees, when segment 210 is deflected.

Figure 2:
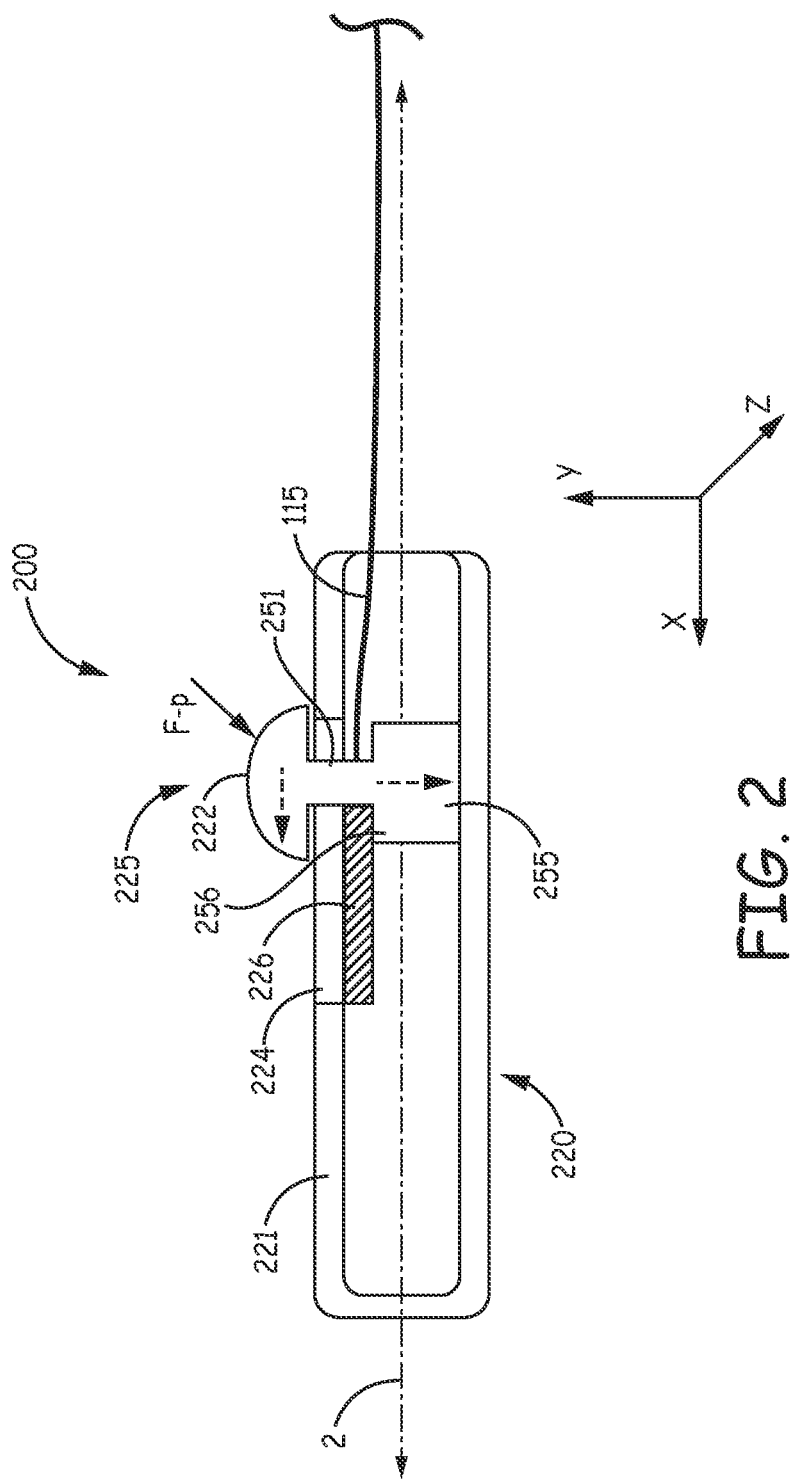
FIG. 2 is a schematic representation of a portion of a deflection assembly, according to some embodiments.

FIG. 2 is a schematic representation of a portion of a shaft deflection assembly 200 for catheter 100, which is useful for defining a frame of reference for the configuration and function of control member subassembly 225, according to some embodiments, in terms of an orthogonal coordinate system of X, Y, and Z axes. FIG. 2 illustrates a proximal end of pull wire 115 secured to a post 251 of subassembly 225 that extends through a slot 224 of a shell 221 of handle 220, and an operator interface 222 coupled to post 251 and located adjacent an outer surface of handle shell 221. Post 251 is shown extending in a vertical direction, generally along the Y axis, which is approximately orthogonal to a length of slot 224 and to a longitudinal axis 2 of handle 220, both extending generally along the X axis.

FIG. 2 further illustrates a force vector F-p, for example, applied by an operator to interface 222 in order to move control member subassembly 225 in a proximal direction along the length of slot 224, which activates pull wire 115 to deflect catheter shaft deflectable segment 210 (FIG. 1B). The force vector F-p is shown having a vertical component along the Y axis and a longitudinal component along the X axis (dashed-line arrows). FIG. 2 also schematically depicts an engagement feature 256 of control member subassembly 225, and a mating feature 226 of handle shell 221, which extends alongside slot 224, wherein engagement feature 256, being supported by an elastically deformable support 255 of subassembly 225, confronts mating feature 226 for interlocking engagement therewith. The vertical component of the illustrated force vector F-p deforms support 255 so that engagement feature 256 moves vertically away from mating feature 226, and out of interlocking engagement therewith, to allow movement in a proximal direction in response to the longitudinal component of the force vector F-p; and, when support 255 is un-deformed, either before the force vector F-p is applied, or after the force vector F-p is released, engagement feature 256 interlocks with mating feature 226 to prevent longitudinal movement of control member subassembly 225 in either direction along the length of handle slot 224. Thus, control member subassembly 225 allows the operator to "pull a curve" in the shaft of catheter 100 with pull wire 115, for example, the 'knuckle' bend shown in FIG. 1C, by moving subassembly 225 proximally, and then allows the operator to release the force vector F-p while control member subassembly 225 still maintains the curve, since, upon release of the force vector F-p, support 255 elastically returns to the un-deformed state, at which engagement feature 256 and mating feature 226 interlock.

Figure 3A:
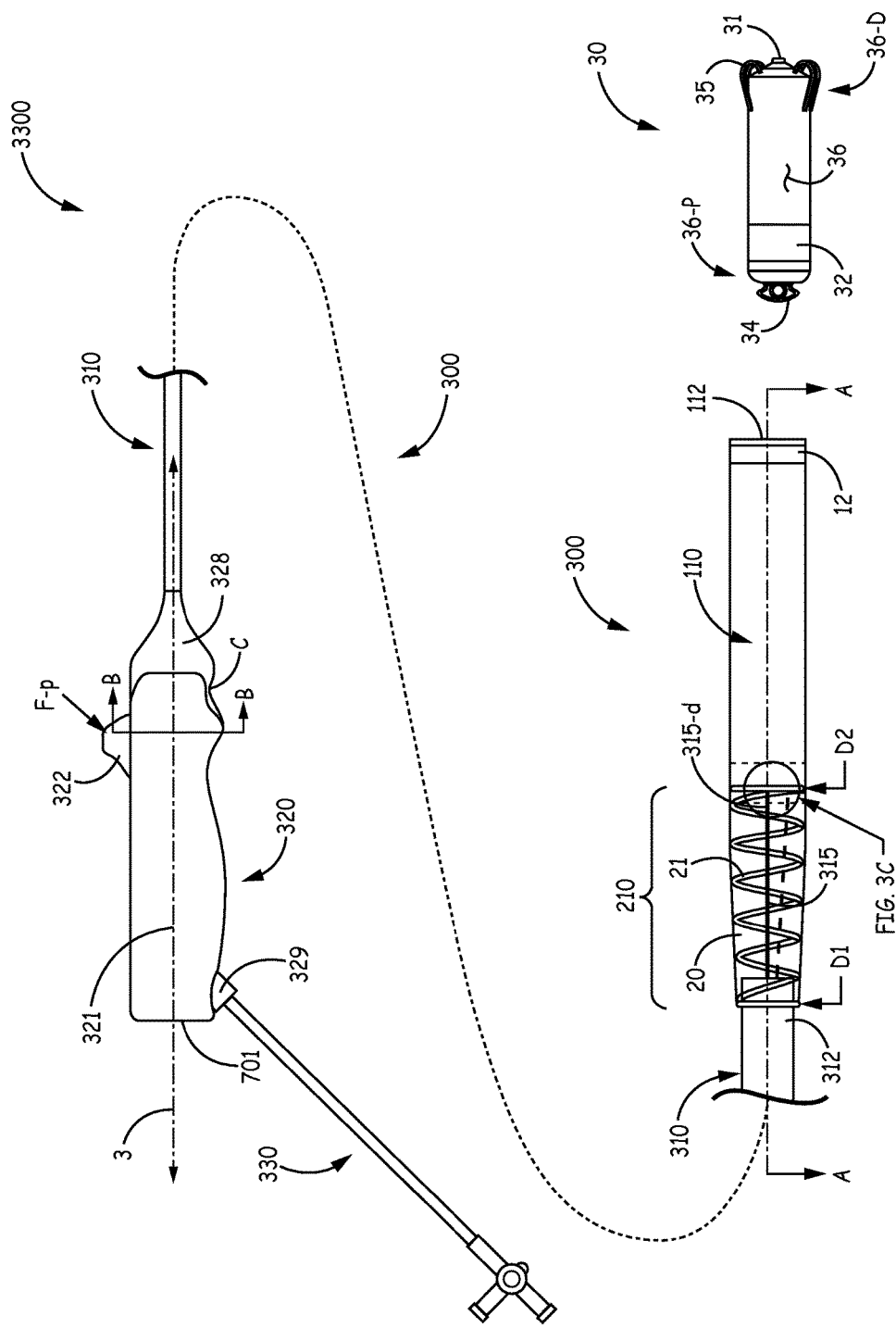
FIG. 3A is a plan view of an interventional medical system, according to some embodiments.

FIG. 3A is a plan view of an interventional medical system 3300, according to some embodiments, wherein an extent of shaft proximal portion 310, between proximal and distal ends of catheter 300, is represented by a dotted line, and implantable medical device 30 of system 3330 is shown positioned and oriented for loading into the above-described distal-most portion 110 of catheter 300. FIG. 3A illustrates catheter 300 including the deflectable shaft of FIG. 1B, wherein shaft proximal portion 310 extends through a strain relief element 328 and is coupled to a handle 320, which is part of a shaft deflection assembly configured for operation in a similar fashion to the schematic description of FIG. 2, according to some embodiments. FIG. 3A further illustrates handle 320 extending along a longitudinal axis 3, and catheter 300 further including a flushing assembly 330, which is connected to a side port 329 of handle 320, and an operator interface 322 of a control member subassembly 325, more of which can be seen in the cross-section view of FIG. 3D. The force vector F-p shown in FIG. 3A, which is similar to that described above, may be applied by a thumb of an operator whose hand grasps around handle 320, for example, with forefingers contacting strain relief element 328 along a surface C thereof.

With further reference to FIG. 3A, in conjunction with FIG. 3B (longitudinal cross-section through section line A-A of FIG. 3A), catheter shaft deflectable segment 210 is shown including a coiled spring member 21 overlaid by a sheath 20, wherein a plurality of open-pitch turns 215 of spring member 21 extend between one or more proximal turns 211 and one or more distal turns 212 of spring member 21, and wherein spring member 21 defines a transition lumen 213 that extends along a longitudinal axis 1 of spring member 21, being in fluid communication with first and second lumens 303, 305 of proximal shaft portion 310 and with receptacle 113 of shaft distal-most portion 110. FIG. 3B shows device 30 having been inserted through distal opening 112 of receptacle 113 for loading into catheter 300, so that a proximal end 36-P of device 30 will abut an internal shoulder 11 of receptacle 113, and fingers of fixation member 35, which are spaced apart from one another around a perimeter of a distal end 36-D of device 30, will be held in an elastically deformed state for deployment out through distal opening 112, once catheter 300 has delivered device 30 to an implant site. According to some exemplary embodiments, shaft distal-most portion 110 has an outer diameter of approximately 0.3 inch (7.6 mm), and receptacle 113 has a diameter of approximately 0.27 inch (7 mm) that extends over a length of approximately 1.3 inches (33 mm) from a location just distal to internal shoulder 11 to distal opening 112. According to the illustrated embodiment, device 30 includes an attachment feature 34 located at proximal end 36-P, which is configured for coupling with a tether member or a snare, or any other similar tool (not shown), for example, that extends through a proximal opening 701 of handle 320 (FIG. 3A) and distally through second lumen 305 and transition lumen 213, so that an operator, by grasping a proximal end of the tool can maintain control over device 30 until device 30 is implanted.

With further reference to FIG. 3B, spring member proximal turns 211 are shown secured to a distal end 312 of shaft proximal portion 310, but, according to some alternate embodiments, proximal turns 211 may be secured to proximal portion 310 at a more proximal location along the length thereof. FIG. 3B further illustrates one or more distal turns 212 of spring member 21 being secured to shaft distal-most portion 110, for example, being coupled to a collar 10 thereof, to which sidewall 101 of distal-most portion 110 is coupled. With further reference to FIGS. 3A-B, pull wire 315 is shown extending within first lumen 303 of shaft proximal portion 310, and alongside coiled spring member 21, and having a distal end 315-d also secured to shaft distal-most portion 110, for example, by attachment to one or more distal turns 212 of spring member 21, as illustrated in the enlarged detail views of FIGS. 3B-C. According to the illustrated embodiment, a sidewall of collar 10 includes a proximal portion 10-p and a distal portion 10-d, wherein one or more distal turns 212 of spring member 21 are mounted around proximal portion 10-p, and an interior of distal portion 10-d forms internal shoulder 11 of shaft distal-most portion 110. According to an exemplary embodiment, sidewall 101 of distal-most portion 110, which may be formed from a medical grade polyether block amide (e.g., PEBAX® 7233 SA-01), extends around and is bonded to distal portion 10-d of collar 10, which may be formed from a relatively hard medical grade plastic such as Polyether ether ketone (PEEK). However, according to some alternate embodiments, collar 10 and sidewall 101 may be integrally formed, either of a relatively rigid medical grade plastic, such as either of the aforementioned, or of a medical grade metal, such as stainless steel, in which case, pull wire distal end 315-d may be secured to distal-most portion 110 by a weld joint.

FIGS. 3B-C illustrate pull wire distal end 315-d extending through an opening 15 formed through sidewall proximal portion 10-p of collar 10, and distal end 315-d being formed in a plurality of loops (alternately, a single loop) that extend around at least one of the one or more distal turns 212 of coiled spring member 21, which are mounted around collar proximal portion 10-p, for attachment thereto. The loops of pull wire distal end 315-d may be press fit within a recess r formed around opening 15 in sidewall proximal portion 10-p of collar 10. According to an exemplary embodiment, pull wire 315 is formed from a medical grade stainless steel wire having a diameter of approximately 0.010 inch, and extends within transition lumen 213, being free to 'float' therein when moved to deflect the catheter shaft (i.e., bend coiled spring member 21). Alternately, if pull wire 315 is formed from a super-elastic material, such as Nitinol, sheath 20 may be formed over pull wire 315 and coiled spring member 21 together, for example, by in-situ molding a medical grade polymer material, such as PEBAX® 3533 SA-01, in which case the above-described fluid communication between transition lumen 213 and first lumen 303 may not exist. In some embodiments, pull wire 315 extends approximately parallel to longitudinal axis 1 of coiled spring member 21, when coiled spring member 21 is unbent, but, in some alternate embodiments, with reference to the dashed lines in FIGS. 3A-B, a distal opening of first lumen 303 at distal end 312 of shaft proximal portion 310 is circumferentially offset from the attached distal end 315-d of pull wire 315, for example, by approximately 45 degrees to 90 degrees. Thus, when pull wire 315 is moved proximally, for example, by an operator applying force vector F-p to operator interface 322 of control member subassembly 325 (FIG. 3A), the resulting bending/deflection of shaft deflectable segment 210 will offset shaft distal-most portion 110 similar to that shown in FIG. 1D.

Figure 9A:
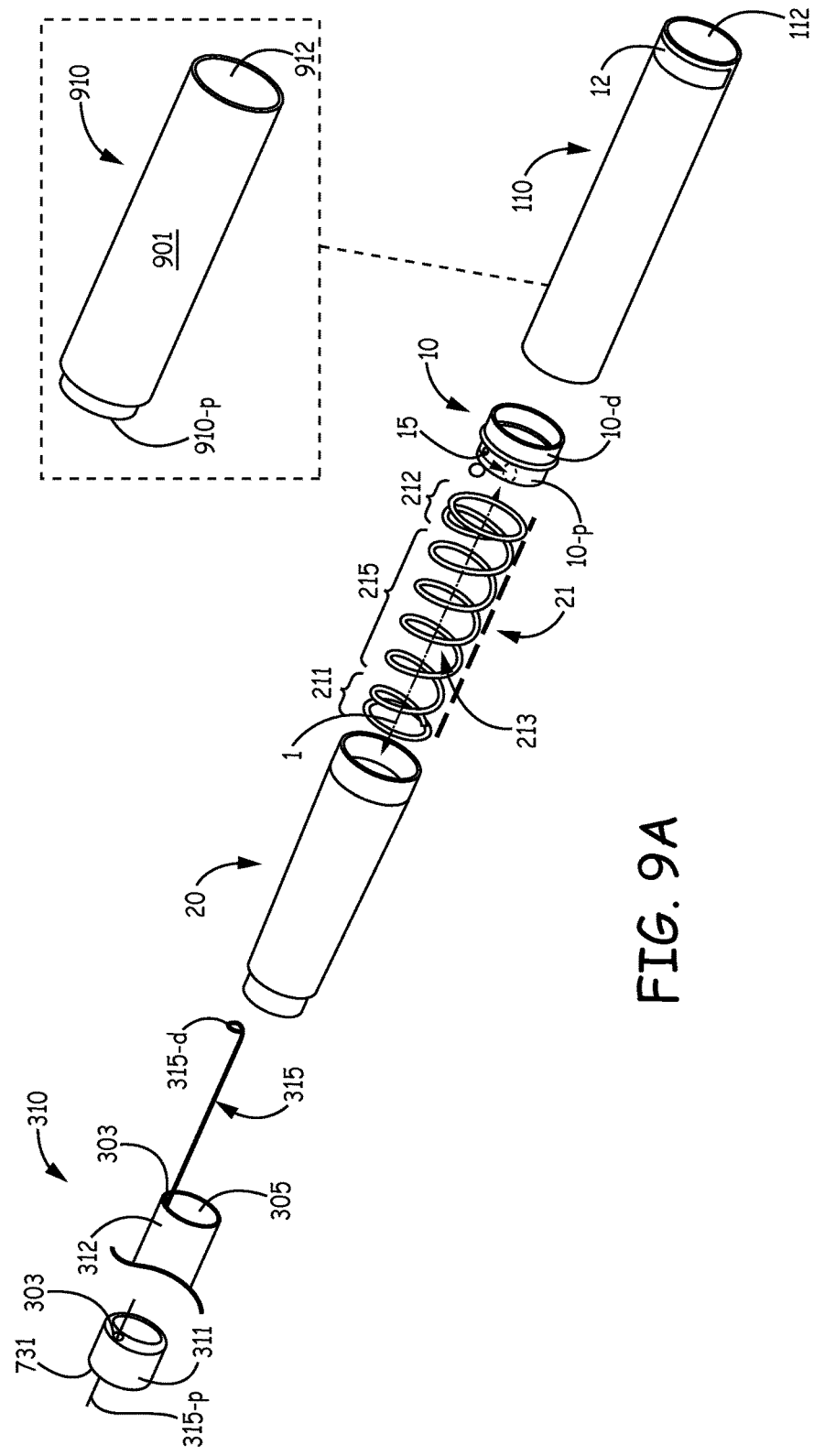
FIG. 9A is an exploded perspective view of a portion of the catheter shown in FIG. 3A, according to some embodiments.

According to some preferred embodiments, one or more proximal turns 211 of coiled spring member 21 have a first diameter D1, and one or more distal turns 212 have a second diameter D2 that is greater than first diameter D1, which may provide more leverage for the proximal movement of pull wire 315 to bend shaft deflectable segment 210, than if diameters D1, D2 were the same. In an exemplary embodiment, first diameter D1 is approximately 0.2 inch (5 mm), and second diameter is approximately 0.25 inch (6.3 mm); however, according to some alternate embodiments, coiled spring member 21 may be isodiametric along an entire length thereof, for example, to facilitate passage of device 30 therethrough if loaded into receptacle 113 from proximal shaft portion 310, rather than through distal opening 112. Furthermore, the plurality of open pitch turns 215 of spring member 21 are preferably compressed, or pre-loaded, along longitudinal axis 1 by sheath 20, for example, to between approximately 10% and 15% of a free length thereof, wherein the free length of spring member 21, which is shown in the exploded perspective view of FIG. 9A, is approximately 1.2 inches (30.5 mm), and the compressed length is approximately 1.0 inch (25.4 mm), according to some exemplary embodiments. Yet sheath 20, for example, formed from a relatively flexible medical grade polymer (e.g., polyester heat shrink tube having a 0.00015 inch wall thickness, or the aforementioned over-molded PEBAX®), allows for some additional longitudinal compression of spring member open pitch turns 215 associated with a bending thereof, which is necessary for the above-described 'knuckle' bend deflection (FIG. 1C) in response to the proximal movement of pull wire 315. According to an exemplary embodiment, coiled spring member 21 tapers outward from diameter D1 to diameter D2 and is wound in a right hand helix from a medical grade stainless steel wire that has a diameter of approximately 0.020 inch (0.5 mm), wherein a pitch of open pitch turns 215, prior to compression/pre-load may be approximately 0.2 inch (5.1 mm).

Methods for constructing the above-described deflectable shaft and integrating the shaft together with the deflection assembly that includes pull wire 315, along with handle 320 and operator interface 322 of FIG. 3A, are described below in conjunction with FIGS. 9A-E and 10A-C.

Figure 3D:
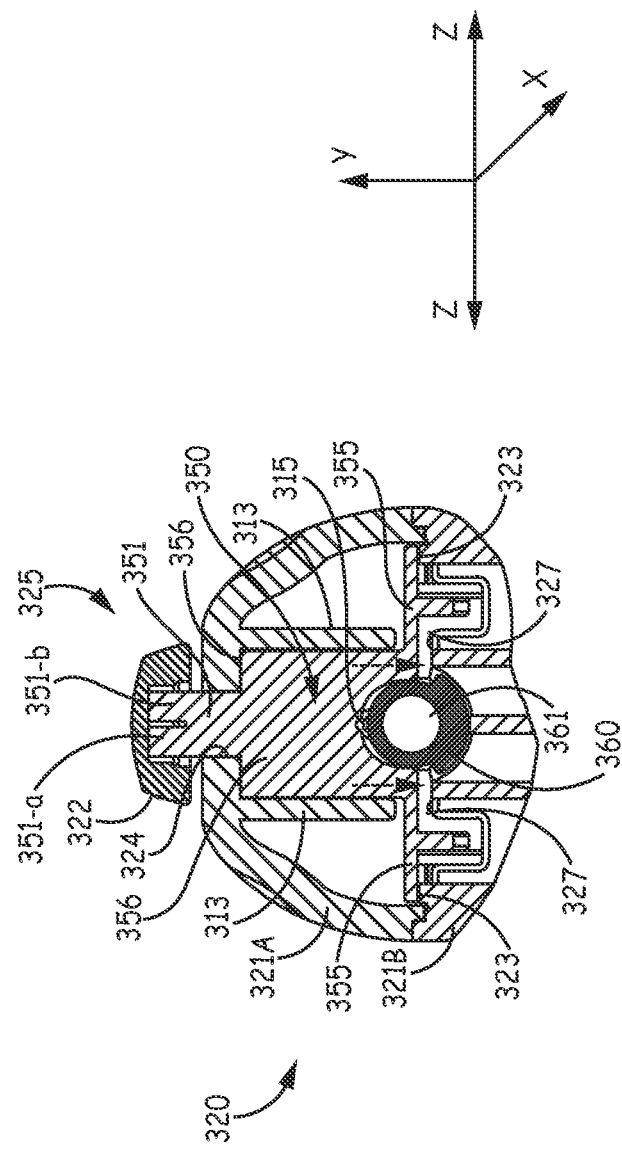
FIG. 3D is a cross-section view through section line B-B of FIG. 3A, according to some embodiments.
Figure 4A:
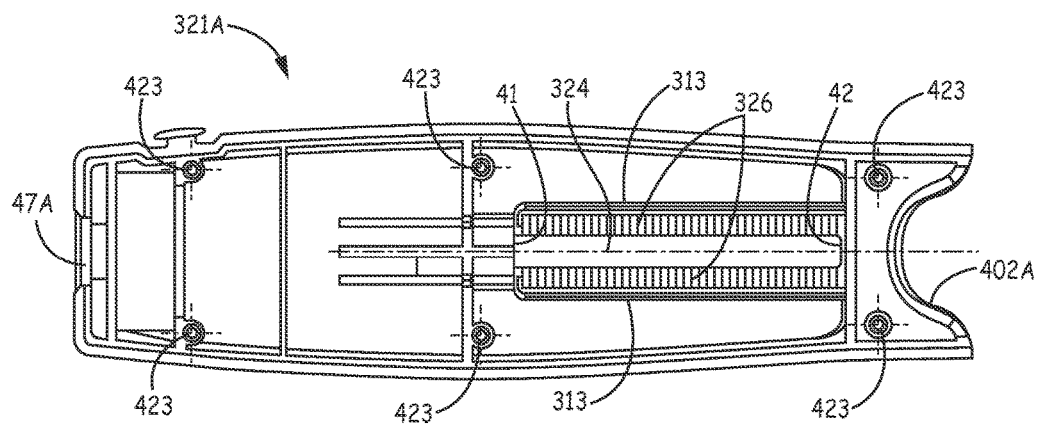
FIGS. 4A-B are plan views of an inner surface of a handle shell, according to some embodiments.
Figure 4B:
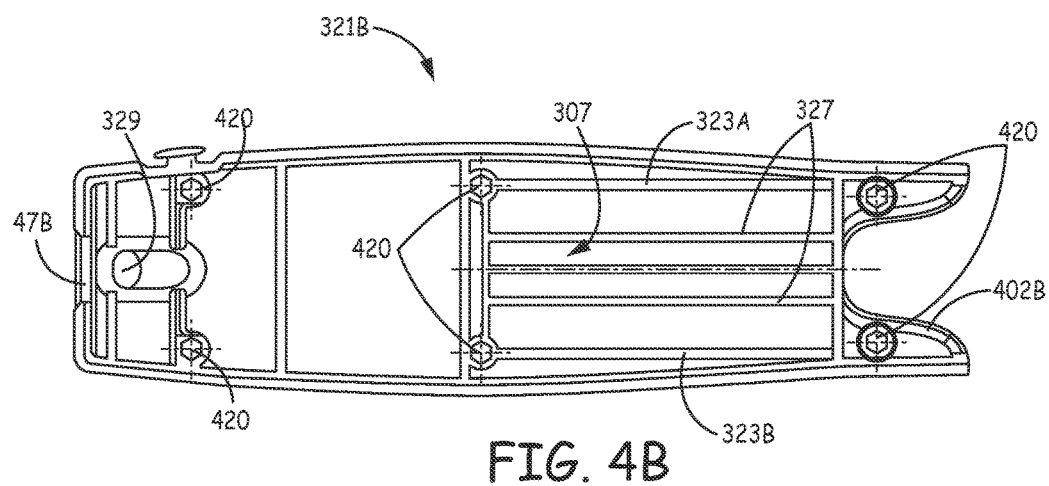

Turning now to FIG. 3D, handle 320 of catheter 300 may be formed by a shell 321 that surrounds a majority of subassembly 325, wherein shell 321 is preferably divided into a first portion 321A and a second portion 321B, plan views of which are shown in FIGS. 4A-B, respectively. FIG. 3D includes the X, Y, Z orthogonal coordinate system (with X axis coming out from the page and corresponding to longitudinal axis 3 of FIG. 3A), to serve as a frame of reference for control member subassembly 325. FIG. 3D illustrates operator interface 322 being in the form of a button member that is secured to a post 351 of subassembly 325. Pull wire 315 of subassembly 325 is secured to post 351, as will be described in greater detail below, and post 351, which is shown being located between first and second engagement features 356 of control member subassembly 325, extends vertically, along the Y axis and through a slot 324 of handle 320. According to the illustrated embodiment, each engagement feature 356 of subassembly 325 confronts a corresponding mating feature of handle shell 321, which may be, for example, a row of teeth 326 formed in inner surface of shell 321 on either side of slot 324, as shown in FIG. 4A. FIG. 3D further illustrates a pair of opposing cantilever beam members 355, which extend generally along the Z axis and form an elastically deformable support of control member subassembly 325. According to some preferred embodiments, post 351, engagement features 356, and the elastically deformable support/beam members 355 are all integrally formed together in a single-piece slider component 350, which will be described in greater detail below, in conjunction with FIGS. 5A-D.

FIG. 3D shows cantilever beam members 355 resting on a railway 323 that protrudes out from the inner surface of handle shell 321; and FIG. 4B illustrates railway 323 being formed by longitudinally extending first and second rails 323A, 323B, each of which supports a corresponding beam member 355, wherein rails 323A, 323B are preferably integrally formed in the inner surface of shell second portion 321B. With further reference to FIG. 3D, beam members 355 bend in response to the vertical component (shown with dashed-line arrows) of the force vector F-p applied to operator interface 322 (FIG. 3A), so that engagement features 356 move out from interlocking engagement with the mating feature of handle (e.g., rows of teeth 326 on either side of slot 324, shown in FIG. 4A), thereby freeing subassembly 325 to move proximally, in response to the longitudinal component of the force vector F-p, along a length of slot 324, which is defined, along the X axis, between a proximal end 41 thereof and a distal end 42 thereof (FIG. 4A). The bending of beam members 355 may be limited by a stop member 327 that protrudes from the inner surface of handle shell 321. FIGS. 3D and 4B illustrate stop member 327, preferably integrally formed in the inner surface of shell second portion 321B, being located in between rails 323A and 323B.

FIGS. 4A-B further illustrate the inner surface of handle shell first portion 321A including a plurality of pin members 423 protruding therefrom, and the inner surface of handle shell second portion 321B including a corresponding plurality of receptacles 420 formed therein, which are configured to receive pin members 423 in a press fit so that perimeter edges of each shell portion 321A, 321B come together in confronting engagement, for example as illustrated in FIG. 3D. With further reference to FIGS. 4A-B, in conjunction with FIG. 3A, a distal edge 402A, 402B of each shell portion 321A, 321B, respectively, is configured to interface with strain relief element 328, as described in greater detail below. According to some exemplary embodiments, handle shell portions 321A, 321B are injection molded from a relatively rigid medical grade plastic, such as Acrylonitrile butadiene styrene (ABS), according to methods known in the art.

FIG. 5A is a perspective view of single-piece slider component 350 of control member subassembly 325, according to some embodiments; and FIGS. 5B-D are elevation, end, and cross-section views of component 350, according to some embodiments. FIG. 5A shows a vertical axis 5 of component 350, which generally corresponds to the Y axis of the orthogonal coordinate system serving as the frame of reference for control member subassembly 325. Along vertical axis 5, upper and lower portions of component 350 are defined. FIGS. 5A-C illustrate the upper portion of component 350 including first and second engagement features 356 and post 351, and the lower portion of component 350 including elastically deformable support/cantilever beam members 355. With reference to FIG. 5C, according to an exemplary embodiment, a thickness t of each cantilever beam member 355 is approximately 0.040 inch; and, in some preferred embodiments, component 350 is injection molded from a medical grade, living-hinge type plastic known to those skilled in the art, for example, nylon, which enhances the above-described elastically deformable support function of beam members 355. FIGS. 5A-D further illustrate the upper portion of slider component 350 including a tail portion 57, and the lower portion of slider component 350 including bumper features 55, both of which are described below in the context of the deflection assembly.

FIGS. 5A and 5C further illustrate component 350 including opposing sidewalls 53, which extend along vertical axis 5 and between the upper and lower portions, and between which an aperture 503 extends, also along axis 5 and between the upper and lower portions. With reference back to FIGS. 3D and 4A, slider component 350 is mounted in first portion 321A of handle shell 321 such that each sidewall 53 thereof is adjacent to a corresponding sidewall 313 of first portion 321A. According to the illustrated embodiment, aperture 503 of slider component 350 allows passage of pull wire proximal end 315-p therethrough (FIG. 6), from shaft proximal portion 310, for securing pull wire 315 to post 351. According to FIGS. 3D, 5A and 5C, post 351 preferably includes a pair of pillars 351-a, 351-b extending side-by-side along vertical axis 5, so that the proximal end of wire 315 may be wrapped around and in between pillars 351-a, 351-b, for example, as described below in conjunction with FIGS. 6 and 9C. Furthermore, in control member subassembly 325, operator interface/button member 322 may be fitted within aperture 503 of component 350, for example, as described below in conjunction with FIGS. 6 and 7.

Figure 6:
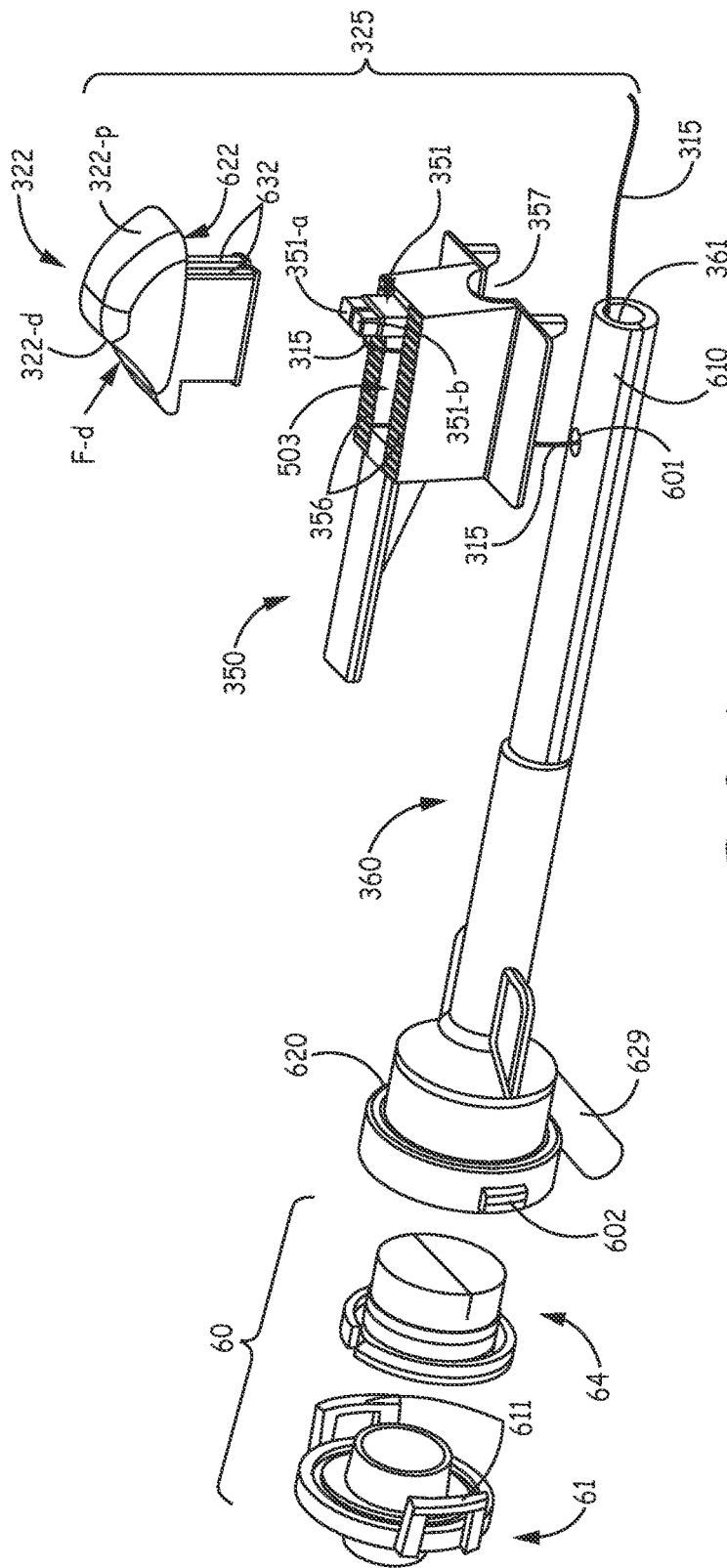
FIG. 6 is an exploded perspective view of a portion of a deflection assembly, according to some embodiments.

FIGS. 5A, 5C and 5D further illustrate the lower portion of slider component 350 including an open channel 357 that extends longitudinally between cantilever beam members 355 and is sized to receive shaft proximal portion 310, or, preferably, a hub 360 of the deflection assembly, as seen in FIG. 3D and further illustrated in the context of the deflection assembly in FIG. 6. According to an exemplary embodiment, hub 360 is formed from a relatively rigid medical grade plastic, for example, polypropylene or polyether block amide. With reference to FIGS. 3D and 6, according to some embodiments, an inner surface of a tubular sidewall of hub 360 defines a lumen 361 that is in fluid communication with first and second lumens 303, 305 of shaft proximal portion 310 (FIG. 3B), wherein a distal end 610 of the tubular sidewall of hub 360 (FIG. 6) may be coupled to a proximal end 311 of proximal portion 310 (FIGS. 7 and 9A), for example, as described below in conjunction with FIGS. 7 and 9A. According to the illustrated embodiment, hub 360 rests on inner surface of second portion 321B of handle shell 321, in a space 307 (FIG. 4B) between protrusions of stop member 327; and control member subassembly 325 is slideably engaged with the tubular sidewall of hub 360, via open channel 357, for movement along the length of slot 324 in response to the longitudinal component of the above-described force vector F-p.

FIGS. 5A, 5B, and 5D further illustrate each of engagement features 356 defined by a longitudinally extending row of teeth formed in a surface of the upper portion of single-piece slider component 350, for example, over a length of approximately 0.91 inch, to interlock with the corresponding row of teeth 326 of handle 320 (FIG. 4A) when component 350 is mounted within handle shell 321, as described above. With reference to the enlarged detail view of FIG. 5D, according to an exemplary embodiment, a pitch p of each row of teeth is approximately 0.050 inch, a height h of each tooth is approximately 0.016 inch, and an angle θ of each tooth is approximately 18 degrees.

FIG. 6 is an exploded perspective view of a portion of the deflection assembly for catheter 300 (FIG. 3A), according to some embodiments. FIG. 6 shows the lower portion of slider component 350 positioned in proximity to distal end 610 of the tubular sidewall of hub 360 for mounting in sliding engagement therewith (e.g., with the tubular sidewall received in open channel 357), and operator interface/button member 322 positioned in proximity to the upper portion of slider component 350 to be fitted together therewith. Button member 322 is shown having a first operator interface surface 322-p, which is oriented to receive application of the above-described force vector F-p (FIG. 3A) that moves control member subassembly 325 in a proximal direction, to 'pull a curve' in the deflectable catheter shaft, and a second operator interface surface 322-d, which is oriented to receive the application of another force vector F-d that has a similar vertical component as that of force vector F, but has a longitudinal component oriented in the opposite direction to move subassembly 325 distally, and thereby straighten the deflectable catheter shaft. FIG. 6 further illustrates pull wire proximal end 315-p extending through an aperture 601 of the tubular sidewall of hub 360, according to some embodiments, and through aperture 503 of component 350, and wrapped around and in between pillars 351-a, 351-b of post 351. According to the illustrated embodiment, and with reference to the longitudinal cross-section view of FIG. 7, legs 632 of button member 322 are configured for a snap fit within aperture 503 so that a cavity 622 of button member 322, which is located beneath surface 322-p, is press fit around pillars 351-a, 351-b, thereby securing pull wire 315 to component 350.

FIG. 6 illustrates hub 360 including another sidewall extending laterally from a proximal end 620 of the aforementioned tubular sidewall to define a side port 629 of hub 360 that, with reference to FIG. 7, extends within the above-referenced side port 329 of handle 320 (FIGS. 3A and 4B). Hub side port 629 provides a means for connecting flushing assembly 330 to handle 320, as described in greater detail below, and, with further reference to FIG. 7, hub side port 629 is in fluid communication with hub lumen 361. FIGS. 6 and 7 further illustrate hub 360 including a valve subassembly 60 that attaches to a proximal opening of hub lumen 361, the proximal opening being defined by proximal end 620 of the tubular sidewall. Valve subassembly 60 is shown including a valve member 64 and a valve cap 61 configured to secure valve member 64 within the proximal opening of hub lumen 361. According to an exemplary embodiment, valve member 64 may formed from medical grade silicone rubber in a slit valve configuration known in the art, which is sized for a press fit within the proximal opening of hub lumen 361. FIG. 6 further illustrates valve cap 61 including a pair of flap members 611, each configured for interlocking with a corresponding laterally protruding feature 602 of hub 360, for example, as shown in FIG. 9E. With reference to FIG. 7, when hub 360 is assembled within handle shell 321, valve subassembly 60 is fitted within proximal opening 701 of handle 320, according to some embodiments. With reference back to FIGS. 4A-B, proximal opening 701 may be formed by opposing proximal edges 47A, 47B of first and second portions 321A, 321B, respectively, of handle shell 321.

FIG. 7 further illustrates proximal end 311 of shaft proximal portion 310, which extends through a lumen 801 of strain relief element 328, inserted within the distal opening of hub lumen 361 for coupling to distal end 610 of hub 360. According to the illustrated embodiment, the inner surface of the tubular sidewall of hub 360 includes a shoulder 761 formed therein and against which a proximal terminal end 731 of shaft proximal portion 310 abuts. In some preferred embodiments, pull wire proximal end 315-p exits from lumen 303 of shaft proximal portion 310 (FIG. 9A) at proximal terminal end 731 to extend through aperture 601 of hub 360, as shown in FIG. 6. But according to some alternate embodiments, shaft proximal portion 310 may include an opening into lumen 303 that is located distal to proximal terminal end 731, so that pull wire 315 exits lumen 303 just distal to distal end 610 of hub 360.

FIG. 8 is a perspective view of strain relief element 328, according to some embodiments. FIG. 8 illustrates strain relief element 328 having an upper edge 802A configured for interlocking with distal edge 402A of shell portion 321A, and a lower edge 802B configured to abut distal edge 402B of second shell portion 321B, which can be seen in FIG. 7. FIG. 8 further illustrates strain relief element 328 including opposing grooves 823 that provide relief for pins 423 of handle shell portion 321A (FIG. 4A), when lumen 801 is fitted around distal end 610 of hub 360, and when edge 802A interfaces with shell portion 321A, as shown in FIGS. 7 and 9B. With further reference to FIG. 7, lower edge 802B of element 328 terminates surface C that fingers of the operator's hand may contact when the operator's thumb applies either one of force vectors F-p, F-d as described above. According to some preferred embodiments, strain relief element 328 is formed from a medical grade thermoplastic elastomer, such as Santoprene™ or Medalist®, for example, by injection molding.

FIG. 9A is an exploded perspective view of the deflectable shaft for catheter 300, embodiments of which are described above in conjunction with FIGS. 3A-C. According to some construction methods, pull wire 315 is inserted within first lumen 303 of shaft proximal portion 310 such that a distal end 315-d thereof protrudes out from a distal opening of lumen 303, at distal end 312 of proximal portion 310, to be attached to one or more distal turns 212 of coiled spring member 21, for example, after inserting distal end 315-d through opening 15 in collar 10 and forming one or more loops in distal end 315-d. With reference to FIG. 9A, sheath 20, spring member 21, and collar 10 may be positioned as illustrated for the threading of pull wire 315 through each, until pull wire distal end 315-d is positioned within an inner surface of sidewall proximal portion 10-p of collar 10, adjacent to opening 15 formed therethrough; then, distal end 315-d may be inserted through opening 15 to an outer surface of sidewall proximal portion 10-p, where the one or more distal turns 212 of coiled spring member 21 can be threaded into the loops of distal end 315-d, as spring member 21 is coupled to collar 10, for example, by being positioned around the outer surface of sidewall proximal portion 10-p, as illustrated in FIGS. 3B-C. With reference back to FIG. 3B, after being attached to coiled spring member 21, the one or more loops of pull wire distal end 315-p may be press fit into recess r formed around opening 15. According to some methods, opening 15 of collar 10 may be oriented, per arrow O, to be circumferentially offset from the distal opening of lumen 303 (as shown with dashed lines), for example, by approximately 45 degrees to 90 degrees, before distal turns 212 of spring member 21 are attached to pull wire distal end 315-p and coupled to collar 10. Distal-most portion 110, which defines receptacle 113 (FIG. 3B), may be coupled to collar 10, for example, being mounted around and bonded, or otherwise secured, to an outer surface of sidewall distal portion 10-d. In some alternate embodiments, as mentioned above, collar 10 and distal-most portion 110 are integrally formed, and FIG. 9A further illustrates, in a dashed-line box, a distal-most portion 910 of such an alternate embodiment. Distal-most portion 910 is shown including a distal opening 912 into a receptacle formed by a sidewall 901 thereof, which has a proximal portion 910-p, to which pull wire distal end 315-d and the one or more distal turns 212 of coiled spring member 21 may be attached, for example, by one or more weld joints, when distal-most portion 910 is formed from a metal, for example, a medical grade stainless steel.

As was described above, in some preferred embodiments, one or more distal turns 212 of coiled spring member 21 have a larger diameter than one or more proximal turns 211 of coiled spring member, so, according to some methods, coiled spring member 21 is initially wound with a tapering diameter to achieve the two diameters (e.g., D1 and D2 of FIGS. 3A-B). In any case, with one or more proximal turns 211 of coiled spring member 21 being coupled to distal end 312 of shaft proximal portion 310, and one or more distal turns 212 being coupled to collar 10, open pitch turns 215 of coiled spring member 21 may be compressed along longitudinal axis 1, for example, approximately 10% to 20% of the illustrated free length, while sheath 20 is moved into position and secured thereabout, for example, by a heat shrink fitting process known in the art. Alternately, as mentioned above, sheath 20 may be formed around the compressed spring member 21 and pull wire 315 by an in-situ over-molding process known in the art; and some steps of shaft construction methods in which in-situ molding is employed are described, below, in conjunction with FIGS. 10A-C. Furthermore, according to some alternate embodiments, spring member 21 may be provided with a backbone member (shown with a dashed line in FIG. 9A), for example, as described in commonly assigned U.S. Pat. No. 6,146,338, wherein the backbone member may be coupled at each end to the one or more proximal turns 211 and to the one or more distal turns 212, for example, by laser welding, and may include longitudinally spaced tabs that extend between adjacent turns of open pitch turns 215. Thus, according to embodiments that include the backbone member, the above-described longitudinal compression of coiled spring member open pitch turns 215 may be secured by the backbone member. The backbone member, when employed, can enhance a stability of shaft deflectable segment 210, for example, by providing a preferred bending direction and by limiting the excess longitudinal compression of open pitch turns 215 during the bending thereof, which may cause distal-most portion 110 to retract relative to the implantable medical device contained in receptacle 113 (FIG. 3A).

With further reference to FIG. 9A, pull wire proximal end 315-p is shown extending out from proximal end 311 of shaft proximal portion 310 for integration into the rest of the deflection assembly, for example, according to some methods described in conjunction with FIGS. 9B-E. The deflectable shaft may be assembled prior to steps schematically depicted in FIGS. 9B-E, but according to some alternate methods, pull wire proximal end 315-p may be partially or completely assembled together with control member subassembly 325 and handle 320 before the above-described steps of the deflectable shaft construction are performed.

FIG. 9B schematically depicts steps 91a, 91b, in which strain relief element 328 is mounted around shaft proximal portion 310, either before or after hub 360 is attached thereto, and in which slider component 350 is mounted in first portion 321A of handle shell 321. According to some methods, hub 360 is over-molded onto proximal end 311 of shaft proximal portion 310, while according to alternate methods, hub 360 is bonded to proximal end 311. The step 91b schematic shows aperture 503 and tail portion 57 of component 350 aligned with handle slot 324, between mating features/rows of teeth 326 of handle shell portion 321A, and open channel 357 of the lower portion of component 350 facing outward from shell portion 321A, so that post 351 extends through slot 324, and so that each engagement feature 356 of the upper portion of component 350 confronts the corresponding mating feature 326 of handle shell portion 321A for the above-described interlocking engagement, which may be seen in part in FIG. 9C. FIG. 9B further illustrates a subsequent assembly step 92, in which hub 360 is mounted in handle shell first portion 321A, being received in open channel 357 of the mounted slider component 350, so that component 350 is in sliding engagement with hub 360, and so that side port 629 of hub 360 extends outward from shell first portion 321A.

Figure 9C:
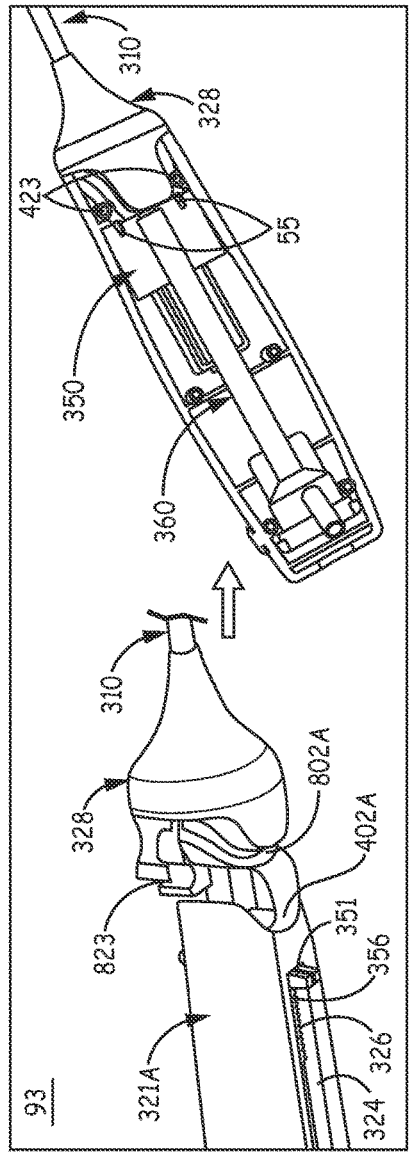

FIG. 9C schematically depicts a subsequent step 93 in which the mounted strain relief element 328 is joined to handle shell first portion 321A by interlocking upper edge 802A of element 328 with distal edge 402A of shell first portion 321A. With further reference to FIG. 9C, grooves 823 of strain relief element 328 can be seen providing the above described relief for pins 423 of first shell portion 321A. Furthermore bumper features 55 of slider component 350 are shown abutting a proximal edge of strain relief element 328, for example, to provide a relatively soft stop to the movement of control subassembly 325 in handle slot 324. It should be noted that no secondary bonding processes need be employed in joining element 328 to handle shell 321, according to the illustrated embodiment.

Figure 9D:
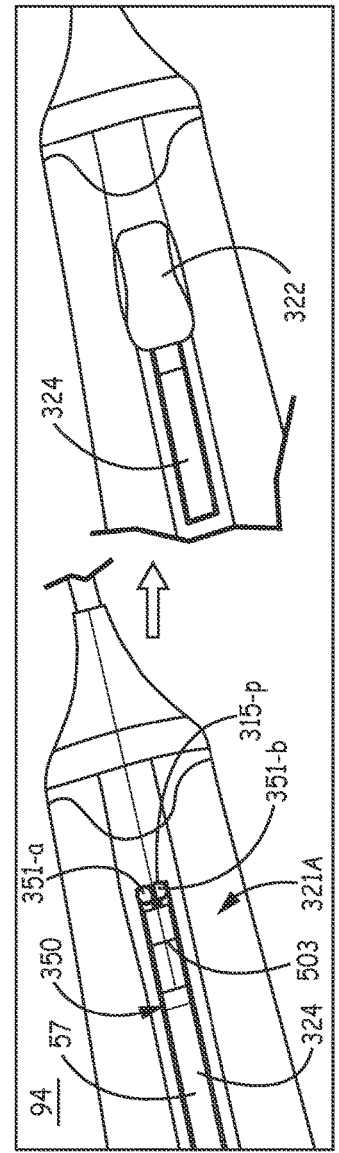
Figure 9E:
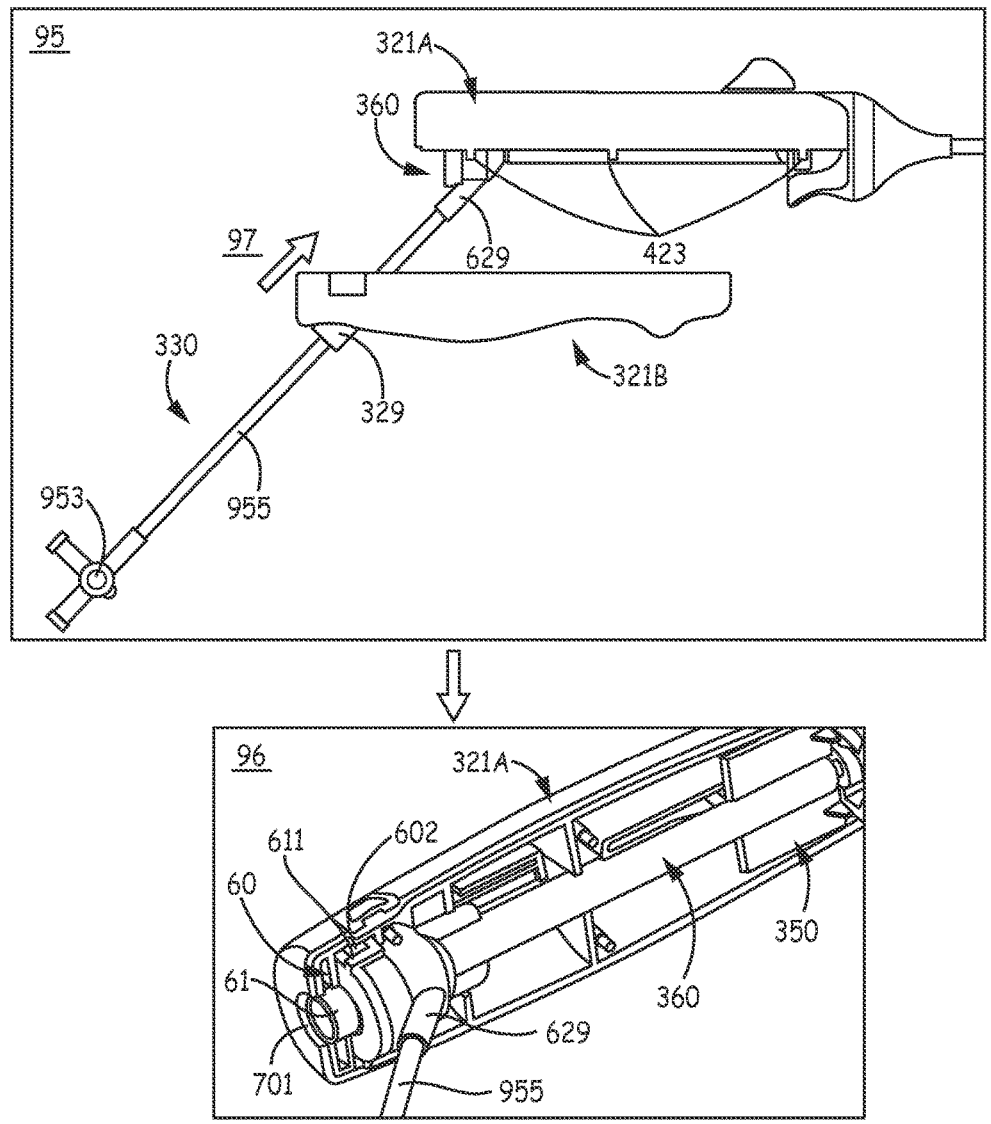

FIG. 9D schematically depicts a subsequent step 94 in which pull wire proximal end 315-p is secured to post 351 of slider component 350. According to some methods, pull wire proximal end 315-p extends out from lumen 303 of shaft proximal portion 310 when the attached hub 316 was mounted in shell portion 321A, per step 92, so that pull wire proximal end 315-p was simultaneously inserted through aperture 503 of component 350. But, according to some alternate methods, pull wire 315 is advanced proximally with lumen 303, so that proximal end 315-p is moved out from lumen 303 during step 94, for insertion through aperture 503. In either case, according to some preferred methods, pull wire proximal end 315-p is wrapped around and between pillars 351-a, 351-b and then button member 322 is fitted around pillars 351-a, 351-b to complete the securing of pull wire 315 to the mounted slider component 350, per step 94. As was described above, button member 322 preferably includes legs 632 that are inserted through slot 324 and snap fitted within aperture 503 of the mounted slider component 350. With further reference to FIG. 9D, tail portion 57 extends along slot 324 to provide a cosmetic cover over an interior of handle shell 321.

FIG. 9E is a schematic depiction of subsequent steps 95, 96, 97 that complete the assembly of the deflection assembly, according to some methods. In step 95 a flush tube 955 of flushing assembly 330 is attached to hub side port 629, for example, by adhesive bonding, and then threaded through side port 329 of handle shell second portion 321B, prior to attaching a stopcock 953 to a free end of tube 955, for example, by adhesive bonding; or stopcock 953 may be attached to tube 955 prior to threading tube 955 through handle side port 329, from an opposite direction, and then attaching tube 955 to side port 629. According to some alternate methods, hub 360 may be over-molded onto flush tube 955 so that tube 955 is already attached to hub 360 when hub 360 is mounted in handle shell first portion 321A at step 92 (FIG. 9B). FIG. 9E shows, in subsequent step 96, valve subassembly 60 mounted to the proximal opening of hub 360, with valve member 64 (FIG. 6) being press fit within the proximal opening of hub 360, and with valve cap 61 fitting within proximal opening 701 of handle shell 321, having flap members 611 interlocking with laterally protruding features 602 of hub 360. The assembly of subassembly 60 together with hub 360 preferably takes place in subsequent step 96 to prevent possible silicone contamination of flush tube 955 bonding site(s) from a silicone lubricant applied to silicone rubber valve member 64. According to the illustrated embodiment, step 96 need not include any bonding of subassembly 60. Finally, in step 97, handle shell portions 321A, 321B are pressed together such that each pin 423 of first portion 321A mates in a press fit with the corresponding receptacle 420 of second portion 321B (FIGS. 4A-B), and handle shell 321 surrounds hub 360, valve subassembly 60, and a majority of control member subassembly 325, for example, as illustrated in FIG. 3A. According to the illustrated embodiment, step 97 need not include any bonding.

Figure 10A:
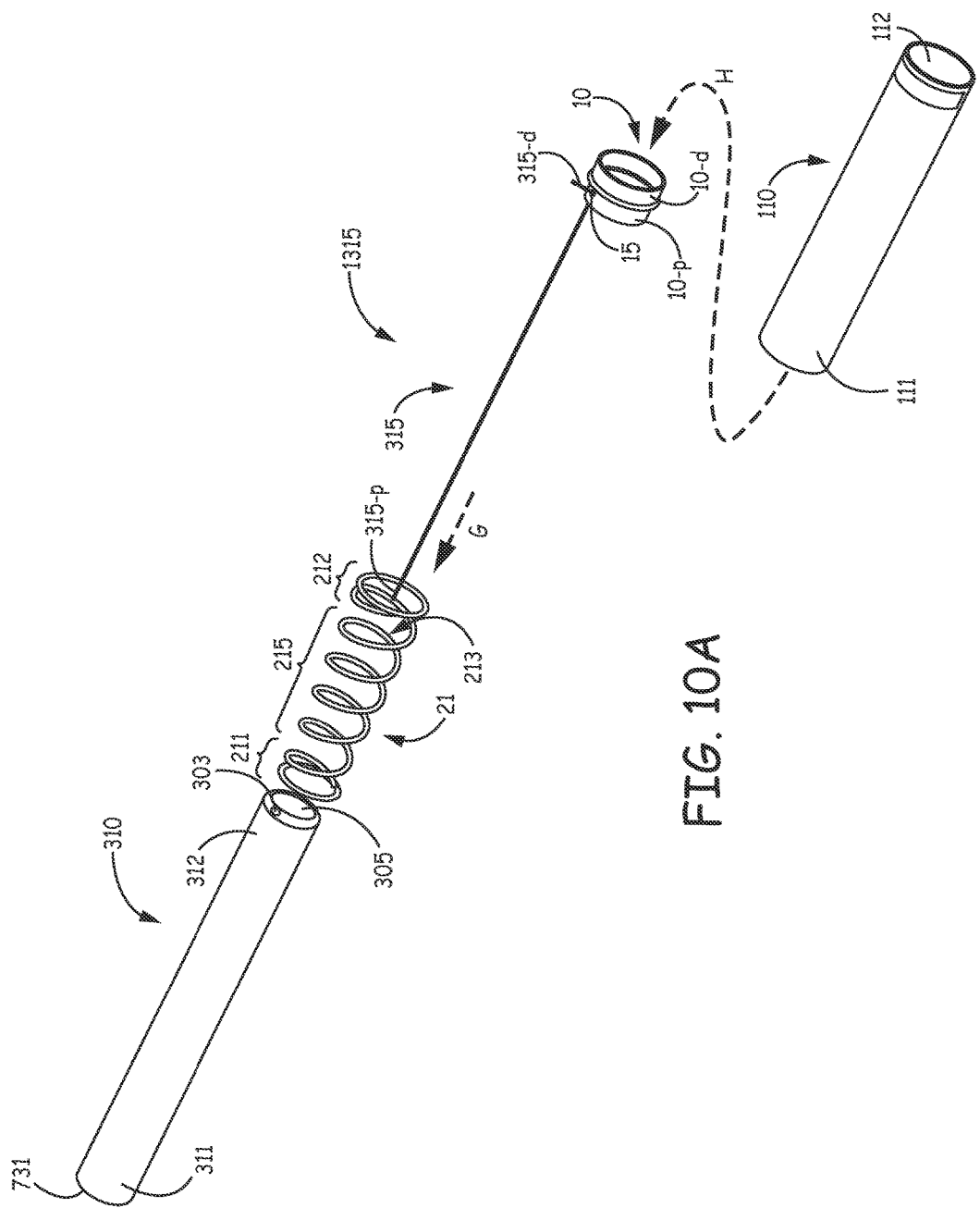

FIGS. 10A-C are schematics outlining some construction methods for a deflectable catheter shaft, for example, embodiments of the shaft employed by catheter 100 (FIGS. 1B-D and 3A). FIG. 10A illustrates one or more proximal turns 211 of coiled spring member 21 positioned in close proximity to distal end 312 of an elongate tubular member (e.g., shaft proximal portion 310), and a subassembly 1315, which may be formed by inserting pull wire distal end 315-d through opening 15 of sidewall proximal portion 10-p of collar 10, positioned for insertion of pull wire 310, per arrow G, through spring member lumen 213 and then through first lumen 303 of tubular member 310. Although not shown, one or more proximal turns 211 of coiled spring member 21 may be positioned around tubular member distal end 312. According to some preferred methods and embodiments, when pull wire 315 is fully inserted, pull wire proximal end 315-p extends proximally from a proximal opening of lumen 303 that is defined by proximal terminal end 731 of tubular member 310, as described above and seen in FIG. 9A, and collar 10 is located adjacent one or more distal turns 212 of coiled spring member 21. With reference back to step 91a of FIG. 9B, according to some embodiments and methods, hub 360, as described above, may be in-situ molded around proximal end 311 of tubular member 315 before inserting pull wire 315 through lumen 303, so that, when fully inserted, pull wire proximal end 315 exits the proximal opening of lumen 303 within hub 360 and then extends out through aperture 601 of hub 360 (FIG. 6). With further reference to FIG. 10A, in a subsequent step, one or more distal turns 212 of spring member 21 are mounted around proximal portion 10-p of the sidewall of collar 10, and a proximal end 111 of a receptacle, for example, receptacle 113 defined by sidewall 101 of distal-most portion 110 (FIGS. 3B and 10C), is positioned around or in close proximity to sidewall distal portion 10-*d* of collar 10, per arrow H.

FIG. 10A further illustrates pull wire distal end 315*d* having been inserted through opening 15 formed through proximal portion 10-*p* of the sidewall of collar 10, according to some methods. With reference back to FIGS. 3B-C, according to some preferred methods and embodiments, pull wire distal end 315*d* is formed in one or more loops through which one or more distal turns 212 of coiled spring member 21 may be inserted for the attachment of pull wire 315 thereto, for example, when spring member distal turns 212 are mounted around proximal portion 10-*p* of the sidewall of collar 10. With further reference to FIGS. 3B-C, according to some methods, the one or more loops of the attached pull wire 315 are then press fit within recess r formed around opening 15.

With reference to FIG. 10B, tubular member 310, subassembly 1315, coiled spring member 21, and receptacle 213 of distal-most portion 110 are shown assembled together, as described above, wherein the assembly, when placed in a mold cavity for in-situ molding to form the above-described sheath 20, according to some preferred methods, may be longitudinally compressed, per arrows C, to pre-load coiled spring member 21, according to some preferred embodiments described above. FIG. 10C is a cross-section view showing in-situ molded sheath 20 extending around an entirety of coiled spring member 21 and overlapping onto tubular member distal end 312, collar 10 and receptacle proximal end 111. Thus, one or more proximal turns 211 of spring member 21 are secured to tubular member 310, transition lumen 213 is enclosed, and one or more distal turns 212 of spring member 21, with pull wire distal end 315-*d* attached thereto, and proximal end 111 of receptacle 213 are secured to pull wire assembly collar 10, so that receptacle 213 is in fluid communication with second lumen 305 of tubular member 310, via lumen 213.

In the foregoing detailed description, the invention has been described with reference to specific embodiments. However, it may be appreciated that various modifications and changes can be made without departing from the scope of the invention as set forth in the appended claims.

The invention claimed is:

1. A catheter for delivering a leadless pacemaker device to an implant site, the catheter comprising:
    an elongate shaft including a proximal portion, a distal-most portion, and a handle, the proximal portion being secured to the handle and including a sidewall that defines first and second lumens extending alongside one another and along a length of the proximal portion, the distal-most portion including an internal shoulder and a sidewall defining a receptacle, the receptacle having a distal opening defined by a distal terminal end of the distal-most portion sidewall, and the receptacle being sized to contain the leadless pacemaker device therein when a proximal end of the leadless pacemaker device abuts the internal shoulder, and the distal opening being sized to allow passage of the leadless pacemaker device therethrough; and
    a coiled spring member including one or more proximal turns secured to the proximal portion of the shaft, one or more distal turns secured to the distal-most portion of the shaft, and a plurality of open-pitch turns therebetween, the spring member defining a transition lumen that extends along a longitudinal axis of the spring member, the transition lumen being in fluid communication with the first and second lumens of the proximal portion of the shaft and the receptacle of the distal-most portion of the shaft, the open-pitch turns being pre-loaded by a longitudinal compression thereof, the one or more proximal turns of the spring member having a first diameter, and the one or more distal turns of the spring member having a second diameter, the second diameter being greater than the first diameter;
    a sheath overlaying the coiled spring member and allowing a bending of the spring member; and
    a deflection assembly including the handle, a control member subassembly, and an elongate pull wire, the pull wire extending from a proximal end thereof to a distal end thereof, and within the first lumen of the proximal portion of the shaft, and alongside the coiled spring member, the distal end of the pull wire being secured to the distal-most portion of the shaft, and the control member subassembly being mounted to the handle and coupled to the proximal end of the pull wire, the control member subassembly being configured to move the pull wire along the length of the proximal portion of the shaft, thereby controlling the bending of the coiled spring member via the pull wire.

2. The catheter of claim 1, wherein a distal opening of the first lumen of the proximal portion of the catheter shaft is located at a distal end of the proximal portion, the distal opening being circumferentially offset from the distal end of the pull wire of the deflection assembly, when the spring member is unbent.

3. The catheter of claim 1, wherein the distal end of the pull wire of the deflection assembly of the catheter is formed in one or more loops, the one or more loops extending around the one or more distal turns of the coiled spring member.

4. The catheter of claim 1, wherein the longitudinal compression of the open-pitch turns of the coiled spring member of the catheter is between 10 percent and 15 percent of a free length of the coiled spring member.

5. The catheter of claim 1, wherein the distal-most portion of the catheter shaft further includes a collar coupled to the sidewall of the distal-most portion, the collar forming the internal shoulder of the distal-most portion, and the one or more distal turns of the coiled spring member being coupled to the collar.

6. The catheter of claim 5, wherein:
    the distal end of the pull wire of the catheter is formed in one or more loops, the one or more loops extending around the one or more distal turns of the coiled spring member; and
    a sidewall of the collar of the distal-most portion of the catheter shaft has a recess formed therein, the one or more loops being press fit within the recess.

7. The catheter of claim 5, wherein a sidewall of the collar has an opening formed therethrough, the distal end of the pull wire extending through the opening of the collar sidewall.

8. The catheter of claim 1, wherein the distal-most portion of the catheter shaft is formed from a medical grade metal material, and the pull wire of the deflection assembly is secured to the shaft distal-most portion by a weld joint.

9. The catheter of claim 1, wherein the coiled spring member of the catheter bends up to 180 degrees in a curve as small as a 5 mm radius, when the control member subassembly of the catheter deflection assembly has moved the pull wire proximally.

10. The system of claim 1, wherein:
the handle of the catheter deflection assembly comprises a shell, first and second rows of teeth, and a railway, the shell having an outer surface, an inner surface, and a slot formed through the shell, the slot having opposing first and second sides and proximal and distal ends defining a length of the slot, the length of the slot extending along a longitudinal axis of the handle, the rows of teeth protruding from the inner surface of the shell, the first row extending alongside the first side of the slot, and the second row extending alongside the second side of the slot, and the railway protruding from the inner surface of the shell, opposite the slot and toward the slot;
the control member subassembly of the catheter deflection assembly comprises a post, to which the proximal end of the pull wire secured, first and second engagement features, an elastically deformable support, and an operator interface coupled to the post, the operator interface being located adjacent the outer surface of the shell, the post being located in between the first and second engagement features and extending through the slot of the shell, each of the first and second engagement features confronting a corresponding row of the first and second rows of teeth of the handle for interlocking engagement therewith, and the elastically deformable support resting on the railway of the handle; and
wherein, when the elastically deformable support of the control member subassembly is un-deformed, each of the first and second engagement features of the control member subassembly interlock with the corresponding row of the first and second rows of teeth, thereby preventing movement of the control member subassembly along the length of the handle slot; and
when a force vector is applied to the operator interface of the control member subassembly, the elastically deformable support deforms against the railway of the handle so that the first and second engagement features of the control member subassembly move out from the interlocking engagement with the first and second rows of teeth of the handle, and the control member subassembly moves along the length of the handle slot, the force vector having a first component directed generally toward the railway and along a vertical axis that is generally orthogonal to the longitudinal axis of the handle, and a second component directed along the longitudinal axis of the handle.

11. The system of claim 10, wherein the first and second rows of teeth and the railway of the deflection assembly handle are integrally formed in the inner surface of the shell.

12. The system of claim 10, wherein:
the elastically deformable support of the control member subassembly comprises first and second flexible cantilever beam members;
the railway of the deflection assembly handle comprises first and second rails extending along the longitudinal axis of the handle, the first rail supporting the first beam member of the control member subassembly, and the second rail supporting the second beam member; and
the deformation of the elastically deformable support in response to the force vector applied to the operator interface comprises a bending of the beam members.

13. The system of claim 12, wherein the deflection assembly handle further comprises a stop member configured to limit the bending of the beam members, the stop member extending along the longitudinal axis of the handle and protruding from the inner surface of the shell in between the first and second rails.

14. The system of claim 10, wherein:
the post of the control member subassembly of the catheter deflection assembly comprises a pair of pillars extending side-by-side and through the slot of the handle shell, the proximal end of the pull wire of the catheter deflection assembly extending therebetween; and
the operator interface of the control member subassembly comprises a button member fitted around the pillars to secure the proximal end of the pull wire therebetween.

15. The system of claim 10, wherein the post, the first and second engagement features, and the elastically deformable support of the control member subassembly of the catheter deflection assembly are all integrally formed together in a single-piece slider component.

16. The system of claim 15, wherein:
the single-piece slider component of the control member subassembly has an upper portion and a lower portion defined along the vertical axis, the upper portion including the first and second engagement features and the post, the lower portion including the elastically deformable support, and the slider component further including a pair of opposing sidewalls extending along the vertical axis, between the upper portion and the lower portion;
each of the first and second engagement features of the slider component comprise a row of teeth formed in a surface of the upper portion of the component; and
the elastically deformable support of the slider component comprises a pair of opposing flexible cantilever beam members, each beam member protruding laterally out from a corresponding sidewall of the pair of opposing sidewalls of the component.

17. The system of claim 16, wherein the single-piece slider component further includes an aperture through which the pull wire extends, the aperture extending between the opposing sidewalls, and along the vertical axis from the upper portion to the lower portion.

18. The system of claim 16, wherein:
the catheter deflection assembly further comprises a hub extending within the handle shell of the deflection assembly and between the first and second rails thereof, the hub including a tubular sidewall that extends from a proximal end thereof to a distal end thereof, an inner surface of the tubular sidewall defining a lumen of the hub, the lumen of the hub having a proximal opening defined by the proximal end of the sidewall and a distal opening defined by the distal end of the sidewall, and the distal end of the tubular sidewall being configured for coupling to a proximal end of the proximal portion of the catheter shaft; and
the lower portion of the single-piece slider component further comprises an open channel that extends between the pair of opposing flexible cantilever beam members and along the longitudinal axis of the handle, the open channel receiving the tubular sidewall of the hub in sliding engagement therewith.

19. The system of claim 10, wherein:
the catheter deflection assembly further comprises a hub extending within the handle shell of the deflection assembly and along the longitudinal axis thereof, the hub including a first sidewall and a second sidewall, the first sidewall defining a lumen of the hub, and the second sidewall defining a side port of the hub, the side port being in fluid communication with the lumen of the hub;

the first sidewall of the hub has a distal end defining a distal opening of the lumen and being configured for coupling to a proximal end of the proximal portion of the catheter shaft; and the handle shell of the deflection assembly further comprises a side port formed therethrough, the side port of the hub extending within the side port of the handle shell.

20. The system of claim 19, wherein the control member subassembly of the catheter deflection assembly is slideably engaged with tubular sidewall of the hub of the deflection assembly.

21. The system of claim 19, wherein:

the hub of the catheter deflection assembly further includes a valve subassembly, the first sidewall of the hub having a proximal end defining a proximal opening of the lumen to which the valve subassembly is attached; and the handle shell of the deflection assembly further comprises a proximal opening formed therethrough, the valve subassembly of the hub being fitted within the proximal opening.

22. The catheter of claim 1, wherein the catheter is configured to contain, of the leadless pacemaker device, an electronic controller and an associated power source, a hermetically sealed housing containing the controller and power source, an electrode electrically coupled to the controller and mounted to the housing, and a fixation member mounted to a distal end of the housing.

\* \* \* \* \*